(12) United States Patent
Christensen et al.

(10) Patent No.: US 9,295,764 B2
(45) Date of Patent: Mar. 29, 2016

(54) CORPOREAL DRAINAGE SYSTEM

(71) Applicant: C. R. Bard, Inc., Murray Hill, NJ (US)

(72) Inventors: Mark A. Christensen, Salt Lake City, UT (US); Steven M. Smith, Sandy, UT (US); Jim C. Beasley, Phoenix, AZ (US); Kelly B. Powers, North Salt Lake, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 14/464,503

(22) Filed: Aug. 20, 2014

(65) Prior Publication Data

US 2014/0358095 A1    Dec. 4, 2014

Related U.S. Application Data

(62) Division of application No. 13/688,000, filed on Nov. 28, 2012, now Pat. No. 8,814,839, which is a division of application No. 11/248,082, filed on Oct. 12, 2005, now Pat. No. 8,337,475.

(60) Provisional application No. 60/617,758, filed on Oct. 12, 2004.

(51) Int. Cl.
*A61M 1/00* (2006.01)
*A61M 3/00* (2006.01)
(Continued)

(52) U.S. Cl.
CPC ........... *A61M 1/0009* (2013.01); *A61M 1/0001* (2013.01); *A61M 1/0011* (2013.01); *A61M 1/0017* (2014.02); *A61M 1/0066* (2013.01); *A61M 1/0072* (2014.02); *B65D 1/0292* (2013.01); *B65D 21/086* (2013.01); *A61M 16/0075* (2013.01); *A61M 39/10* (2013.01); *A61M 2202/0492* (2013.01);
(Continued)

(58) Field of Classification Search
CPC ............ A61M 1/0001; A61M 1/0066; A61M 1/0072; A61M 16/0075; A61M 2205/075; A61M 1/0023; Y10S 206/825; Y10S 206/829; Y10S 493/94
See application file for complete search history.

(56) References Cited

U.S. PATENT DOCUMENTS

| 2,547 | A | 4/1842 | Welchman |
| 11,623 | A | 8/1854 | Waters |

(Continued)

FOREIGN PATENT DOCUMENTS

| CA | 2546434 C | 1/2013 |
| DE | 1616493 A1 | 6/1971 |

(Continued)

OTHER PUBLICATIONS

U.S. Appl. No. 11/248,082, filed Oct. 12, 2005 Advisory Action dated May 21, 2012.

(Continued)

*Primary Examiner* — Adam Marcetich
(74) *Attorney, Agent, or Firm* — Rutan & Tucker, LLP

(57) ABSTRACT

A corporeal drainage system and a method of draining fluid from a bodily cavity. The corporeal drainage system includes a connection tube and a fluid receptacle in fluid communication with the connection tube. The fluid receptacle creates a negative pressure in the system by transitioning from a collapsed configuration to an expanded configuration. The system may include an activation member to initiate transitioning of the fluid receptacle.

6 Claims, 10 Drawing Sheets

(51) Int. Cl.
  *B65D 1/02* (2006.01)
  *B65D 21/08* (2006.01)
  *A61M 39/10* (2006.01)
  *A61M 16/00* (2006.01)
  *B65D 37/00* (2006.01)

(52) U.S. Cl.
  CPC ........... *A61M 2205/75* (2013.01); *B65D 37/00* (2013.01); *Y10S 206/825* (2013.01); *Y10S 206/829* (2013.01); *Y10S 215/90* (2013.01); *Y10S 297/08* (2013.01); *Y10S 493/94* (2013.01)

(56) References Cited

U.S. PATENT DOCUMENTS

| | | |
|---|---|---|
| 44,843 A | 10/1864 | Smith |
| 1,177,208 A | 3/1916 | Pierpont |
| 1,197,232 A | 9/1916 | Pierpont |
| 2,397,257 A | 3/1946 | Goland et al. |
| 3,003,500 A | 10/1961 | Barton et al. |
| 3,021,841 A | 2/1962 | Burke |
| 3,058,627 A | 10/1962 | Eskridge |
| 3,115,138 A | 12/1963 | McElvenny et al. |
| 3,223,610 A | 12/1965 | Inoue |
| 3,233,610 A | 2/1966 | Wade |
| 3,241,554 A | 3/1966 | Coanda |
| 3,253,594 A | 5/1966 | Matthews |
| 3,312,221 A | 4/1967 | Overment |
| 3,315,802 A | 4/1967 | Lonholdt et al. |
| 3,319,684 A | 5/1967 | Calhoun |
| 3,340,869 A * | 9/1967 | Bane .................... 600/578 |
| 3,363,626 A | 1/1968 | Bidwell et al. |
| 3,376,868 A | 4/1968 | Mondiadis |
| 3,417,750 A | 12/1968 | Carson |
| 3,419,010 A | 12/1968 | Williamson |
| 3,459,189 A | 8/1969 | Alley |
| 3,487,837 A | 1/1970 | Petersen |
| 3,542,026 A | 11/1970 | Bledsoe |
| 3,554,580 A | 1/1971 | Goyke |
| 3,566,875 A | 3/1971 | Stoehr |
| 3,572,340 A | 3/1971 | Lloyd et al. |
| 3,650,507 A | 3/1972 | Nyberg et al. |
| 3,680,562 A | 8/1972 | Wittes et al. |
| 3,683,929 A | 8/1972 | Holter |
| 3,742,952 A | 7/1973 | Magers et al. |
| 3,752,158 A | 8/1973 | Kariher |
| 3,768,476 A | 10/1973 | Raitto |
| 3,774,611 A | 11/1973 | Tussey et al. |
| 3,777,757 A | 12/1973 | Gray et al. |
| 3,783,870 A | 1/1974 | Schachet |
| 3,809,087 A | 5/1974 | Lewis, Jr. |
| 3,820,546 A | 6/1974 | Chittenden et al. |
| 3,853,127 A | 12/1974 | Spademan |
| 3,875,941 A | 4/1975 | Adair |
| 3,920,023 A | 11/1975 | Dye et al. |
| 3,960,153 A | 6/1976 | Carey et al. |
| 3,982,546 A | 9/1976 | Friend |
| 3,994,032 A * | 11/1976 | Spickofsky .................. 4/255.11 |
| 4,022,209 A | 5/1977 | Nehring |
| 4,029,095 A | 6/1977 | Pena |
| 4,073,294 A | 2/1978 | Stanley et al. |
| 4,105,031 A | 8/1978 | Kurtz et al. |
| 4,112,949 A | 9/1978 | Rosenthal et al. |
| 4,116,366 A | 9/1978 | Takenakashima et al. |
| 4,120,715 A | 10/1978 | Ockwell et al. |
| 4,136,696 A | 1/1979 | Nehring |
| 4,143,853 A | 3/1979 | Abramson |
| 4,153,058 A | 5/1979 | Nehme |
| 4,170,300 A | 10/1979 | Pick |
| 4,174,053 A | 11/1979 | Shimizu |
| 4,187,848 A | 2/1980 | Taylor |
| 4,203,445 A | 5/1980 | Jessup et al. |
| 4,214,593 A | 7/1980 | Imbruce et al. |
| 4,257,629 A | 3/1981 | Maple et al. |
| 4,265,848 A | 5/1981 | Rusch et al. |
| 4,266,355 A | 5/1981 | Moss |
| 4,266,545 A | 5/1981 | Moss |
| 4,310,104 A | 1/1982 | Takatsuki |
| 4,315,513 A | 2/1982 | Nawash et al. |
| 4,334,551 A | 6/1982 | Pfister |
| 4,341,212 A | 7/1982 | Medwid |
| D267,433 S | 12/1982 | Pageau |
| 4,364,395 A | 12/1982 | Redmond et al. |
| D267,815 S | 2/1983 | Elliott et al. |
| 4,382,442 A | 5/1983 | Jones |
| 4,392,858 A | 7/1983 | George et al. |
| 4,393,873 A | 7/1983 | Nawash et al. |
| 4,402,682 A | 9/1983 | Garver, Sr. et al. |
| 4,427,425 A | 1/1984 | Briggs et al. |
| 4,429,693 A | 2/1984 | Blake et al. |
| 4,433,973 A | 2/1984 | Kurtz et al. |
| 4,439,190 A | 3/1984 | Protzmann et al. |
| 4,447,235 A | 5/1984 | Clarke |
| 4,455,141 A | 6/1984 | Todd |
| 4,464,168 A | 8/1984 | Redmond et al. |
| 4,475,904 A | 10/1984 | Wang |
| 4,479,818 A | 10/1984 | Briggs et al. |
| 4,490,003 A | 12/1984 | Robinson |
| 4,496,464 A | 1/1985 | Hensley |
| 4,501,363 A | 2/1985 | Isbey, Jr. |
| 4,511,163 A | 4/1985 | Harris et al. |
| 4,512,771 A | 4/1985 | Norton |
| 4,525,167 A | 6/1985 | Goldberg et al. |
| 4,539,985 A | 9/1985 | Magrath |
| 4,543,100 A | 9/1985 | Brodsky |
| 4,564,222 A | 1/1986 | Loker et al. |
| 4,569,674 A | 2/1986 | Phillips et al. |
| 4,583,972 A | 4/1986 | Hunter, III et al. |
| 4,605,400 A | 8/1986 | Kurtz et al. |
| 4,610,469 A | 9/1986 | Wolff-Mooij |
| 4,610,671 A | 9/1986 | Luther |
| 4,620,846 A | 11/1986 | Goldberg et al. |
| 4,642,088 A | 2/1987 | Gunter |
| 4,643,720 A | 2/1987 | Lanciano |
| 4,648,870 A | 3/1987 | Goldberg et al. |
| 4,666,433 A | 5/1987 | Parks |
| 4,669,463 A | 6/1987 | McConnell |
| 4,673,398 A | 6/1987 | Turner et al. |
| 4,675,020 A | 6/1987 | McPhee |
| 4,681,571 A | 7/1987 | Nehring |
| 4,685,901 A | 8/1987 | Parks |
| 4,685,908 A | 8/1987 | Kurtz |
| 4,701,163 A | 10/1987 | Parks |
| 4,702,733 A | 10/1987 | Wright et al. |
| 4,706,830 A | 11/1987 | Wareing et al. |
| 4,722,735 A | 2/1988 | Brodmann |
| 4,738,671 A | 4/1988 | Elliott et al. |
| 4,740,202 A | 4/1988 | Stacey et al. |
| 4,741,678 A | 5/1988 | Nehring |
| 4,747,843 A | 5/1988 | Felix et al. |
| 4,747,844 A | 5/1988 | Elliott |
| 4,752,292 A | 6/1988 | Lopez et al. |
| 4,758,238 A | 7/1988 | Sundblom et al. |
| 4,781,674 A | 11/1988 | Redmond et al. |
| 4,790,567 A | 12/1988 | Kawano et al. |
| 4,809,679 A | 3/1989 | Shimonaka et al. |
| 4,813,929 A | 3/1989 | Semrad |
| 4,820,288 A | 4/1989 | Isono |
| 4,828,546 A | 5/1989 | McNeil et al. |
| 4,832,442 A | 5/1989 | Pappas |
| 4,834,702 A | 5/1989 | Rocco |
| 4,844,087 A | 7/1989 | Garg |
| 4,850,955 A | 7/1989 | Newkirk |
| 4,857,042 A | 8/1989 | Schneider |
| 4,863,593 A | 9/1989 | Quick |
| 4,867,740 A | 9/1989 | East |
| 4,874,377 A | 10/1989 | Newgard et al. |
| 4,883,474 A | 11/1989 | Sheridan et al. |
| 4,883,476 A | 11/1989 | Kurtz et al. |
| 4,921,488 A | 5/1990 | Maitz et al. |
| 4,928,830 A | 5/1990 | Brewer |
| 4,929,235 A | 5/1990 | Merry et al. |
| 4,930,997 A | 6/1990 | Bennett |
| 4,944,732 A | 7/1990 | Russo |

(56) References Cited

U.S. PATENT DOCUMENTS

| | | |
|---|---|---|
| 4,946,448 A | 8/1990 | Richmond |
| 4,946,449 A | 8/1990 | Davis, Jr. |
| 4,949,756 A | 8/1990 | Melinyshyn et al. |
| 4,950,256 A | 8/1990 | Luther et al. |
| 4,960,412 A | 10/1990 | Fink |
| 4,966,197 A | 10/1990 | Jaron et al. |
| 4,968,294 A | 11/1990 | Salama |
| 4,969,879 A | 11/1990 | Lichte |
| 4,969,890 A | 11/1990 | Sugita et al. |
| 4,973,311 A | 11/1990 | Iwakoshi et al. |
| 4,981,474 A | 1/1991 | Bopp et al. |
| 4,995,864 A | 2/1991 | Bartholomew et al. |
| 5,002,528 A | 3/1991 | Palestrant |
| 5,002,529 A | 3/1991 | Cunningham |
| 5,009,226 A | 4/1991 | Holt |
| 5,009,635 A | 4/1991 | Scarberry |
| 5,009,636 A | 4/1991 | Wortley et al. |
| 5,019,059 A * | 5/1991 | Goldberg et al. ............. 604/317 |
| 5,019,096 A | 5/1991 | Fox, Jr. et al. |
| 5,024,653 A | 6/1991 | Kohnke |
| 5,037,403 A | 8/1991 | Garcia |
| 5,052,998 A | 10/1991 | Zimmon |
| 5,053,014 A | 10/1991 | Van Heugten |
| 5,057,084 A | 10/1991 | Ensminger et al. |
| 5,060,833 A | 10/1991 | Edison et al. |
| 5,061,255 A | 10/1991 | Greenfeld et al. |
| 5,062,835 A | 11/1991 | Maitz et al. |
| 5,064,416 A | 11/1991 | Newgard et al. |
| 5,078,677 A | 1/1992 | Gentelia et al. |
| 5,078,689 A | 1/1992 | Keller |
| 5,078,699 A | 1/1992 | Haber et al. |
| 5,085,349 A | 2/1992 | Fawcett |
| 5,092,850 A | 3/1992 | Buma |
| 5,098,405 A | 3/1992 | Peterson et al. |
| 5,100,394 A | 3/1992 | Dudar et al. |
| 5,102,404 A | 4/1992 | Goldberg et al. |
| 5,106,054 A | 4/1992 | Mollenauer et al. |
| 5,112,323 A | 5/1992 | Winkler et al. |
| 5,137,524 A | 8/1992 | Lynn et al. |
| 5,141,499 A | 8/1992 | Zappacosta |
| 5,156,597 A | 10/1992 | Verreet et al. |
| 5,165,953 A | 11/1992 | Shlenker et al. |
| 5,188,622 A | 2/1993 | Muller et al. |
| 5,199,946 A | 4/1993 | Abramowitz |
| 5,207,655 A | 5/1993 | Sheridan |
| 5,215,538 A | 6/1993 | Larkin |
| 5,234,454 A | 8/1993 | Bangs |
| 5,238,217 A | 8/1993 | Fell |
| 5,242,422 A * | 9/1993 | Schneberger ....... A61M 3/0262 222/206 |
| 5,251,873 A | 10/1993 | Atkinson et al. |
| 5,261,897 A | 11/1993 | Kurtz et al. |
| 5,269,771 A | 12/1993 | Thomas et al. |
| 5,279,551 A | 1/1994 | James |
| 5,279,601 A | 1/1994 | Lichte |
| 5,295,657 A | 3/1994 | Atkinson |
| 5,295,658 A | 3/1994 | Atkinson et al. |
| 5,300,034 A | 4/1994 | Behnke et al. |
| 5,300,048 A | 4/1994 | Drewes, Jr. et al. |
| 5,304,121 A | 4/1994 | Sahatjian |
| 5,309,924 A | 5/1994 | Peabody |
| 5,320,110 A | 6/1994 | Wang |
| 5,322,518 A | 6/1994 | Schneider et al. |
| 5,330,447 A | 7/1994 | Barth |
| 5,334,159 A | 8/1994 | Turkel |
| 5,334,166 A | 8/1994 | Palestrant |
| 5,344,401 A | 9/1994 | Radisch et al. |
| 5,345,929 A | 9/1994 | Jansson et al. |
| 5,352,198 A | 10/1994 | Goldenberg et al. |
| 5,356,391 A | 10/1994 | Stewart |
| 5,360,413 A | 11/1994 | Leason et al. |
| 5,390,898 A | 2/1995 | Smedley et al. |
| 5,395,651 A | 3/1995 | Sodervall et al. |
| 5,399,165 A | 3/1995 | Paul, Jr. |
| 5,401,245 A | 3/1995 | Haining |
| 5,403,284 A | 4/1995 | Gross |
| 5,405,331 A | 4/1995 | Behnke et al. |
| 5,407,434 A | 4/1995 | Gross |
| 5,423,334 A | 6/1995 | Jordan |
| 5,435,470 A | 7/1995 | Kim |
| 5,437,900 A | 8/1995 | Kuzowski |
| 5,456,675 A | 10/1995 | Wolbring et al. |
| 5,465,857 A | 11/1995 | Yang |
| 5,470,319 A | 11/1995 | Mayer |
| 5,472,325 A | 12/1995 | Svendsen |
| 5,472,435 A | 12/1995 | Sutton |
| 5,480,392 A | 1/1996 | Mous |
| 5,484,401 A | 1/1996 | Rodriguez et al. |
| 5,489,269 A | 2/1996 | Aldrich et al. |
| 5,492,304 A | 2/1996 | Smith et al. |
| 5,496,299 A | 3/1996 | Felix et al. |
| 5,501,426 A | 3/1996 | Atkinson et al. |
| 5,505,717 A | 4/1996 | Moore |
| 5,507,733 A | 4/1996 | Larkin et al. |
| 5,507,847 A | 4/1996 | George et al. |
| 5,509,433 A | 4/1996 | Paradis |
| 5,509,909 A | 4/1996 | Moy |
| 5,509,912 A | 4/1996 | Vaillancourt et al. |
| 5,514,117 A | 5/1996 | Lynn |
| 5,520,665 A | 5/1996 | Fleetwood |
| 5,529,278 A | 6/1996 | Weldon et al. |
| 5,535,785 A | 7/1996 | Werge et al. |
| 5,540,661 A | 7/1996 | Tomisaka et al. |
| 5,556,387 A | 9/1996 | Mollenauer et al. |
| 5,573,516 A | 11/1996 | Tyner |
| 5,576,072 A | 11/1996 | Hostettler et al. |
| 5,597,536 A | 1/1997 | Mayer |
| 5,628,735 A | 5/1997 | Skow |
| 5,628,908 A | 5/1997 | Kamen et al. |
| 5,636,875 A | 6/1997 | Wasser et al. |
| 5,637,103 A | 6/1997 | Kerwin et al. |
| 5,662,960 A | 9/1997 | Hostettler et al. |
| 5,674,192 A | 10/1997 | Sahatjian et al. |
| 5,676,346 A | 10/1997 | Leinsing |
| D385,889 S | 11/1997 | Kullas et al. |
| 5,685,866 A | 11/1997 | Lopez |
| 5,690,612 A | 11/1997 | Lopez et al. |
| 5,695,466 A | 12/1997 | Lopez et al. |
| 5,701,934 A | 12/1997 | Kuran et al. |
| 5,709,672 A | 1/1998 | Illner |
| 5,725,506 A | 3/1998 | Freeman et al. |
| 5,727,714 A | 3/1998 | Fawcett |
| 5,733,496 A | 3/1998 | Avellanet |
| 5,735,826 A | 4/1998 | Richmond |
| 5,738,144 A | 4/1998 | Rogers |
| 5,738,656 A | 4/1998 | Wagner et al. |
| 5,745,719 A | 4/1998 | Falcon et al. |
| 5,746,719 A | 5/1998 | Farra et al. |
| 5,776,119 A | 7/1998 | Bilbo et al. |
| 5,792,098 A | 8/1998 | Felix et al. |
| 5,792,108 A | 8/1998 | Felix et al. |
| 5,807,348 A | 9/1998 | Zinger et al. |
| 5,810,792 A | 9/1998 | Fangrow, Jr. et al. |
| 5,813,597 A | 9/1998 | Wakevainen |
| 5,814,024 A | 9/1998 | Thompson et al. |
| 5,823,961 A | 10/1998 | Fields et al. |
| 5,830,185 A | 11/1998 | Block, Jr. |
| 5,839,715 A | 11/1998 | Leinsing |
| 5,873,853 A | 2/1999 | Keilman et al. |
| 5,897,782 A | 4/1999 | Chatelin et al. |
| 5,904,334 A | 5/1999 | Grunert et al. |
| 5,921,233 A * | 7/1999 | Gold et al. ............... 128/200.22 |
| 5,921,972 A | 7/1999 | Skow |
| 5,937,885 A | 8/1999 | Sampson |
| 5,938,176 A | 8/1999 | Falconer |
| 5,944,703 A | 8/1999 | Dixon et al. |
| 5,947,953 A | 9/1999 | Ash et al. |
| 5,954,313 A | 9/1999 | Ryan |
| 5,954,706 A | 9/1999 | Sahatjian |
| 5,957,898 A | 9/1999 | Jepson et al. |
| 5,957,912 A | 9/1999 | Heitzmann |
| 5,961,497 A | 10/1999 | Larkin |
| 5,971,357 A | 10/1999 | Denton et al. |
| 5,972,441 A | 10/1999 | Campbell et al. |

(56) References Cited

U.S. PATENT DOCUMENTS

| | | |
|---|---|---|
| 5,976,650 A | 11/1999 | Campbell et al. |
| 5,984,891 A | 11/1999 | Keilman et al. |
| 5,997,486 A | 12/1999 | Burek et al. |
| 6,001,079 A | 12/1999 | Pourchez |
| 6,004,116 A * | 12/1999 | Wang ........................ 417/480 |
| 6,024,731 A | 2/2000 | Seddon et al. |
| 6,025,044 A | 2/2000 | Campbell et al. |
| 6,027,779 A | 2/2000 | Campbell et al. |
| 6,027,811 A | 2/2000 | Campbell et al. |
| 6,029,946 A | 2/2000 | Doyle |
| 6,039,302 A | 3/2000 | Cote, Sr. et al. |
| 6,039,714 A | 3/2000 | Cracauer et al. |
| 6,056,730 A | 5/2000 | Greter |
| 6,056,731 A | 5/2000 | Koetke et al. |
| 6,063,062 A | 5/2000 | Paradis |
| 6,068,011 A | 5/2000 | Paradis |
| 6,070,767 A | 6/2000 | Gardner et al. |
| 6,079,444 A | 6/2000 | Harris et al. |
| 6,089,541 A | 7/2000 | Weinheimer et al. |
| 6,093,154 A | 7/2000 | Burek et al. |
| 6,103,695 A | 8/2000 | Lane et al. |
| 6,106,502 A | 8/2000 | Richmond |
| 6,106,503 A | 8/2000 | Pfeiderer et al. |
| 6,113,068 A | 9/2000 | Ryan |
| 6,117,114 A | 9/2000 | Paradis |
| 6,120,264 A * | 9/2000 | Wang ........................ 417/480 |
| 6,129,699 A | 10/2000 | Haight et al. |
| 6,129,750 A | 10/2000 | Tockman et al. |
| 6,132,403 A | 10/2000 | Lopez |
| 6,132,407 A | 10/2000 | Genese et al. |
| 6,149,129 A | 11/2000 | Harris et al. |
| 6,156,004 A | 12/2000 | Tremaine et al. |
| 6,165,217 A | 12/2000 | Hayes |
| 6,168,137 B1 | 1/2001 | Paradis |
| 6,170,800 B1 | 1/2001 | Meloul et al. |
| 6,171,287 B1 | 1/2001 | Lynn et al. |
| 6,193,682 B1 | 2/2001 | Ahmed |
| 6,196,992 B1 | 3/2001 | Keilman et al. |
| 6,200,292 B1 | 3/2001 | French et al. |
| 6,217,556 B1 | 4/2001 | Ellingson et al. |
| 6,221,425 B1 | 4/2001 | Michal et al. |
| 6,234,992 B1 | 5/2001 | Haight et al. |
| 6,235,009 B1 | 5/2001 | Skow |
| 6,245,048 B1 | 6/2001 | Fangrow, Jr. et al. |
| 6,254,061 B1 | 7/2001 | Levine et al. |
| 6,254,581 B1 | 7/2001 | Scott |
| 6,261,276 B1 | 7/2001 | Reitsma |
| 6,261,282 B1 | 7/2001 | Jepson et al. |
| 6,283,949 B1 | 9/2001 | Roorda |
| 6,287,285 B1 | 9/2001 | Michal et al. |
| 6,293,929 B1 | 9/2001 | Smith et al. |
| 6,299,131 B1 | 10/2001 | Ryan |
| 6,299,593 B1 | 10/2001 | Wakabayashi |
| 6,309,423 B2 | 10/2001 | Hayes |
| 6,319,235 B1 * | 11/2001 | Yoshino ............... A61B 5/1405 604/212 |
| 6,328,765 B1 | 12/2001 | Hardwick et al. |
| 6,332,892 B1 | 12/2001 | Desmond, III et al. |
| 6,344,033 B1 | 2/2002 | Jepson et al. |
| 6,352,525 B1 | 3/2002 | Wakabayashi |
| 6,375,024 B1 | 4/2002 | Park |
| 6,391,009 B1 | 5/2002 | Crosa Dorado et al. |
| 6,409,716 B1 | 6/2002 | Sahatjian et al. |
| 6,428,520 B1 | 8/2002 | Lopez et al. |
| 6,447,473 B1 | 9/2002 | Levine et al. |
| 6,468,190 B1 | 10/2002 | Fazio et al. |
| 6,482,190 B1 | 11/2002 | Genese et al. |
| 6,491,668 B1 | 12/2002 | Paradis |
| 6,500,164 B1 | 12/2002 | Turner et al. |
| 6,530,951 B1 | 3/2003 | Bates et al. |
| 6,541,116 B2 | 4/2003 | Michal et al. |
| 6,551,267 B1 | 4/2003 | Cohen et al. |
| 6,554,808 B1 | 4/2003 | Cook |
| 6,562,013 B1 | 5/2003 | Marasco, Jr. |
| RE38,145 E | 6/2003 | Lynn |
| 6,620,132 B1 | 9/2003 | Skow |
| 6,626,418 B2 | 9/2003 | Kiehne et al. |
| 6,634,384 B2 | 10/2003 | Skeens et al. |
| 6,635,020 B2 | 10/2003 | Tripp, Jr. et al. |
| 6,637,726 B1 | 10/2003 | Yamamoto |
| 6,641,562 B1 | 11/2003 | Peterson |
| 6,641,574 B2 | 11/2003 | Badia Segura et al. |
| 6,645,547 B1 | 11/2003 | Shekalim et al. |
| 6,651,956 B2 | 11/2003 | Miller |
| 6,652,484 B1 | 11/2003 | Hunckler et al. |
| 6,655,655 B1 | 12/2003 | Matkovich et al. |
| 6,656,517 B2 | 12/2003 | Michal et al. |
| 6,665,888 B1 | 12/2003 | Kwak |
| 6,669,681 B2 | 12/2003 | Jepson et al. |
| 6,673,049 B2 | 1/2004 | Hommann et al. |
| 6,673,051 B2 | 1/2004 | Flinchbaugh |
| 6,695,817 B1 | 2/2004 | Fangrow, Jr. |
| 6,699,213 B1 | 3/2004 | Annis et al. |
| 6,706,022 B1 | 3/2004 | Leinsing et al. |
| 6,708,950 B2 | 3/2004 | Christensen et al. |
| 6,719,991 B2 | 4/2004 | Darouiche et al. |
| 6,726,672 B1 | 4/2004 | Hanly et al. |
| 6,730,107 B2 | 5/2004 | Kelley et al. |
| 6,733,000 B2 | 5/2004 | McCarty et al. |
| 6,733,481 B2 | 5/2004 | Ow |
| 6,745,998 B2 | 6/2004 | Doyle |
| 6,755,391 B2 | 6/2004 | Newton et al. |
| 6,780,497 B1 | 8/2004 | Walter |
| 6,802,836 B2 | 10/2004 | Bouphavichith et al. |
| 6,808,161 B1 | 10/2004 | Hishikawa |
| D500,132 S | 12/2004 | Peterson et al. |
| D500,133 S | 12/2004 | Peterson et al. |
| D500,552 S | 1/2005 | Peterson et al. |
| D500,853 S | 1/2005 | Peterson et al. |
| 6,840,501 B2 | 1/2005 | Doyle |
| 6,849,061 B2 | 2/2005 | Wagner |
| 6,889,437 B2 | 5/2005 | Bader et al. |
| 6,896,665 B2 | 5/2005 | Picha et al. |
| 6,897,349 B2 | 5/2005 | Gibbins et al. |
| 6,916,379 B2 | 7/2005 | Shekalim et al. |
| 6,936,031 B2 | 8/2005 | Caleffi |
| 6,972,001 B2 | 12/2005 | Emig et al. |
| 6,994,315 B2 | 2/2006 | Ryan et al. |
| 6,994,325 B2 | 2/2006 | Riedl |
| 7,004,923 B2 | 2/2006 | Deniega et al. |
| 7,004,934 B2 | 2/2006 | Vaillancourt |
| 7,008,407 B1 | 3/2006 | Kamp |
| 7,044,441 B2 | 5/2006 | Doyle |
| 7,048,724 B2 | 5/2006 | Grossman et al. |
| 7,048,962 B2 | 5/2006 | Shekalim et al. |
| 7,052,603 B2 | 5/2006 | Schick |
| 7,090,191 B2 | 8/2006 | Matkovich et al. |
| 7,094,218 B2 | 8/2006 | Rome et al. |
| 7,100,890 B2 | 9/2006 | Cote, Sr. et al. |
| 7,101,353 B2 | 9/2006 | Lui et al. |
| 7,112,177 B2 | 9/2006 | Christensen et al. |
| 7,147,138 B2 | 12/2006 | Shelton, IV |
| 7,150,740 B2 | 12/2006 | Bennett et al. |
| 7,163,495 B2 | 1/2007 | Fazio et al. |
| 7,165,568 B2 | 1/2007 | Kessell et al. |
| 7,179,244 B2 | 2/2007 | Smith et al. |
| 7,184,825 B2 | 2/2007 | Leinsing et al. |
| 7,207,946 B2 | 4/2007 | Sirokman |
| 7,303,553 B2 | 12/2007 | Ott |
| 7,311,690 B2 | 12/2007 | Burnett |
| 7,312,304 B2 | 12/2007 | Coy et al. |
| 7,314,061 B2 | 1/2008 | Peppel |
| 7,320,674 B2 | 1/2008 | Ruddell et al. |
| 7,341,240 B2 | 3/2008 | Ciesielka |
| 7,377,915 B2 | 5/2008 | Rasmussen et al. |
| 7,383,073 B1 | 6/2008 | Abovitz et al. |
| 7,396,348 B2 | 7/2008 | Newton et al. |
| 7,401,703 B2 | 7/2008 | McMichael et al. |
| 7,452,346 B2 | 11/2008 | Axelsson |
| 7,452,354 B2 | 11/2008 | Bright et al. |
| 7,468,058 B2 | 12/2008 | Kanie et al. |
| 7,497,848 B2 | 3/2009 | Leinsing et al. |
| 7,497,849 B2 | 3/2009 | Fangrow, Jr. |
| 7,524,311 B2 | 4/2009 | Phung et al. |

(56) References Cited

U.S. PATENT DOCUMENTS

| | | |
|---|---|---|
| 7,530,546 B2 | 5/2009 | Ryan et al. |
| 7,547,302 B2 | 6/2009 | Porto et al. |
| 7,563,243 B2 | 7/2009 | Mendels |
| 7,569,045 B2 | 8/2009 | Deniega et al. |
| 7,578,803 B2 | 8/2009 | Rome et al. |
| 7,584,767 B2 | 9/2009 | Funamura et al. |
| 7,591,805 B2 | 9/2009 | Lampropoulos |
| 7,594,910 B2 | 9/2009 | Butts et al. |
| 7,611,503 B2 | 11/2009 | Spohn et al. |
| 7,614,123 B2 | 11/2009 | Schweikert |
| 7,621,903 B2 | 11/2009 | DeLegge |
| 7,628,774 B2 | 12/2009 | Fangrow, Jr. |
| 7,628,779 B2 | 12/2009 | Aneas |
| 7,632,260 B2 | 12/2009 | Antoine |
| 7,637,893 B2 | 12/2009 | Christensen et al. |
| 7,644,722 B2 | 1/2010 | Christensen et al. |
| 7,674,248 B2 | 3/2010 | Anderson et al. |
| 7,678,092 B2 | 3/2010 | Matloub et al. |
| 7,682,332 B2 | 3/2010 | Tanaka |
| 7,691,090 B2 | 4/2010 | Belley et al. |
| 7,695,458 B2 | 4/2010 | Belley et al. |
| 7,708,027 B2 | 5/2010 | Yokota et al. |
| 7,717,891 B1 | 5/2010 | Whaley |
| 7,726,315 B2 | 6/2010 | Field |
| 7,726,328 B2 | 6/2010 | Christensen et al. |
| 7,736,336 B2 | 6/2010 | Plishka et al. |
| 7,744,594 B2 | 6/2010 | Yamazaki et al. |
| 7,766,304 B2 | 8/2010 | Phillips |
| 7,766,938 B2 | 8/2010 | McGurk et al. |
| 7,798,974 B2 | 9/2010 | Sirokman |
| 7,815,168 B2 | 10/2010 | Vangsness et al. |
| 7,824,384 B2 | 11/2010 | Watson, Jr. |
| 7,833,194 B2 | 11/2010 | Owens et al. |
| 7,854,731 B2 | 12/2010 | Rome et al. |
| 7,857,284 B2 | 12/2010 | Kimball et al. |
| 7,867,204 B2 | 1/2011 | Bartholomew et al. |
| 7,879,012 B2 | 2/2011 | Kane et al. |
| 7,892,181 B2 | 2/2011 | Christensen et al. |
| 7,924,255 B2 | 4/2011 | Hsu et al. |
| 8,007,257 B2 | 8/2011 | Heaton et al. |
| 8,048,046 B2 | 11/2011 | Hudspeth et al. |
| 8,048,056 B2 | 11/2011 | Picha et al. |
| 8,052,671 B2 | 11/2011 | Christensen et al. |
| 8,057,448 B2 | 11/2011 | Williams et al. |
| 8,074,848 B2 | 12/2011 | Pittl et al. |
| 8,083,332 B2 | 12/2011 | Price et al. |
| 8,177,772 B2 | 5/2012 | Christensen et al. |
| 8,210,166 B2 | 7/2012 | Denton et al. |
| 8,224,422 B2 | 7/2012 | Mottola et al. |
| 8,235,971 B2 | 8/2012 | Christensen et al. |
| 8,246,590 B2 | 8/2012 | Hu et al. |
| 8,337,475 B2 | 12/2012 | Christensen et al. |
| 8,435,221 B2 | 5/2013 | Hu et al. |
| 8,636,721 B2 | 1/2014 | Alam et al. |
| 8,814,839 B2 | 8/2014 | Christensen et al. |
| 2001/0047158 A1* | 11/2001 | Ladd ............................ 604/316 |
| 2002/0002351 A1 | 1/2002 | Cote et al. |
| 2002/0148467 A1 | 10/2002 | Bosse et al. |
| 2002/0153503 A1 | 10/2002 | Newton et al. |
| 2002/0198458 A1 | 12/2002 | Tripp et al. |
| 2003/0017920 A1 | 1/2003 | Fazio et al. |
| 2003/0032940 A1 | 2/2003 | Doyle |
| 2003/0040769 A1 | 2/2003 | Kelley et al. |
| 2003/0111121 A1 | 6/2003 | Skeens et al. |
| 2003/0165647 A1 | 9/2003 | Kaneko et al. |
| 2003/0173536 A1 | 9/2003 | Christensen et al. |
| 2004/0049157 A1 | 3/2004 | Plishka et al. |
| 2004/0078026 A1 | 4/2004 | Wagner |
| 2004/0082923 A1 | 4/2004 | Field |
| 2004/0116894 A1 | 6/2004 | DeLegge |
| 2004/0209801 A1 | 10/2004 | Brand et al. |
| 2004/0215155 A1 | 10/2004 | Wolfe et al. |
| 2004/0267163 A1 | 12/2004 | Opie et al. |
| 2005/0000975 A1 | 1/2005 | Carco et al. |
| 2005/0025816 A1 | 2/2005 | Tanaka |
| 2005/0080387 A1* | 4/2005 | Matsuura et al. ............. 604/317 |
| 2005/0090805 A1 | 4/2005 | Shaw et al. |
| 2005/0121638 A1 | 6/2005 | Doyle |
| 2005/0131357 A1 | 6/2005 | Denton et al. |
| 2005/0143691 A1 | 6/2005 | Picha et al. |
| 2005/0203463 A1 | 9/2005 | Lampropoulos |
| 2005/0203597 A1 | 9/2005 | Yamazaki et al. |
| 2005/0209572 A1 | 9/2005 | Rome et al. |
| 2005/0209581 A1 | 9/2005 | Butts et al. |
| 2005/0251102 A1 | 11/2005 | Hegland et al. |
| 2005/0261636 A1 | 11/2005 | Rome et al. |
| 2005/0261664 A1 | 11/2005 | Rome et al. |
| 2005/0267445 A1 | 12/2005 | Mendels |
| 2005/0267487 A1 | 12/2005 | Christensen et al. |
| 2005/0281822 A1 | 12/2005 | Cedarbaum et al. |
| 2006/0009801 A1 | 1/2006 | McGurk et al. |
| 2006/0015086 A1 | 1/2006 | Rasmussen et al. |
| 2006/0025816 A1 | 2/2006 | Shelton |
| 2006/0058702 A1 | 3/2006 | Christensen et al. |
| 2006/0079853 A1 | 4/2006 | Christensen et al. |
| 2006/0092109 A1 | 5/2006 | Hsu et al. |
| 2006/0116721 A1 | 6/2006 | Yun et al. |
| 2006/0118749 A1 | 6/2006 | Ryan et al. |
| 2006/0129109 A1 | 6/2006 | Shaw et al. |
| 2006/0200089 A1 | 9/2006 | Lopez et al. |
| 2006/0211998 A1 | 9/2006 | Fangrow |
| 2006/0211999 A1 | 9/2006 | Fangrow |
| 2006/0212000 A1 | 9/2006 | Fangrow |
| 2006/0212001 A1 | 9/2006 | Fangrow |
| 2006/0212002 A1 | 9/2006 | Fangrow |
| 2006/0212003 A1 | 9/2006 | Fangrow |
| 2006/0264842 A1 | 11/2006 | Fangrow |
| 2007/0038143 A1 | 2/2007 | Christensen et al. |
| 2007/0073270 A1 | 3/2007 | Christensen et al. |
| 2007/0083157 A1 | 4/2007 | Belley et al. |
| 2007/0083162 A1 | 4/2007 | O'Reagan et al. |
| 2007/0100295 A1 | 5/2007 | Belley et al. |
| 2007/0100322 A1 | 5/2007 | Venugopalan et al. |
| 2007/0100324 A1 | 5/2007 | Tempel et al. |
| 2007/0235674 A1 | 10/2007 | Vangsness et al. |
| 2007/0235675 A1 | 10/2007 | Kimball et al. |
| 2007/0235676 A1 | 10/2007 | Vangsness et al. |
| 2007/0255167 A1 | 11/2007 | Christensen et al. |
| 2007/0255229 A1 | 11/2007 | Kane et al. |
| 2007/0260195 A1 | 11/2007 | Bartholomew et al. |
| 2007/0270764 A1 | 11/2007 | Gordon |
| 2007/0282268 A1 | 12/2007 | Mayse |
| 2008/0091174 A1 | 4/2008 | Alam et al. |
| 2008/0097407 A1 | 4/2008 | Plishka |
| 2008/0103408 A1 | 5/2008 | Denton et al. |
| 2008/0114316 A1 | 5/2008 | Christensen et al. |
| 2008/0177175 A1 | 7/2008 | Mottola et al. |
| 2008/0277610 A1 | 11/2008 | Bahner et al. |
| 2009/0012493 A1 | 1/2009 | Harig |
| 2009/0043270 A1 | 2/2009 | Noyce et al. |
| 2009/0069763 A1 | 3/2009 | DiCarlo et al. |
| 2009/0142741 A1 | 6/2009 | Ault et al. |
| 2009/0219353 A1 | 9/2009 | Price et al. |
| 2009/0261130 A1 | 10/2009 | Pittl et al. |
| 2009/0312725 A1 | 12/2009 | Braga |
| 2009/0314973 A1 | 12/2009 | Christensen et al. |
| 2010/0030163 A1 | 2/2010 | Carrez et al. |
| 2010/0044609 A1 | 2/2010 | Matsubara |
| 2010/0274229 A1 | 10/2010 | Duocastella Codina et al. |
| 2011/0009849 A1 | 1/2011 | Christensen et al. |
| 2011/0022012 A1 | 1/2011 | Kerr et al. |
| 2011/0071415 A1 | 3/2011 | Karwoski et al. |
| 2011/0083665 A1 | 4/2011 | Denton et al. |
| 2011/0105963 A1 | 5/2011 | Hu et al. |
| 2011/0172510 A1 | 7/2011 | Chickering, III et al. |
| 2011/0238022 A1 | 9/2011 | Massi et al. |
| 2011/0275964 A1 | 11/2011 | Greener |
| 2011/0276017 A1 | 11/2011 | Schuessler et al. |
| 2012/0220984 A1 | 8/2012 | Christensen et al. |
| 2013/0090614 A1 | 4/2013 | Christensen et al. |
| 2014/0182594 A1 | 7/2014 | Alam et al. |

(56) References Cited

U.S. PATENT DOCUMENTS

FOREIGN PATENT DOCUMENTS

| | | | |
|---|---|---|---|
| DE | 9105229 | U1 | 6/1991 |
| DE | 4311715 | A1 | 10/1994 |
| EP | 0270205 | A2 | 6/1988 |
| EP | 0829248 | A2 | 3/1998 |
| EP | 1547537 | A1 | 6/2005 |
| EP | 1740253 | A1 | 1/2007 |
| EP | 1782850 | A1 | 5/2007 |
| FR | 2551978 | A2 | 3/1985 |
| GB | 2394761 | A | 5/2004 |
| JP | 2002-049660 | A | 2/1990 |
| JP | 2005-115556 | A | 5/1993 |
| JP | H6-504468 | T | 5/1994 |
| JP | H6-66642 | | 9/1994 |
| JP | 2000-517216 | A | 12/2000 |
| JP | 2002-177379 | A | 6/2002 |
| WO | 9003194 | A1 | 4/1990 |
| WO | 9207591 | A1 | 5/1992 |
| WO | 9501135 | A1 | 1/1995 |
| WO | 9911192 | A1 | 3/1999 |
| WO | 0204065 | A2 | 1/2002 |
| WO | 03001993 | A2 | 1/2003 |
| WO | 03018105 | A1 | 3/2003 |
| WO | 2005007213 | A2 | 1/2005 |
| WO | 2005044716 | A2 | 5/2005 |
| WO | 2005052366 | A2 | 6/2005 |
| WO | 2005099805 | A1 | 10/2005 |
| WO | 2005107843 | A1 | 11/2005 |
| WO | 2006004943 | A2 | 1/2006 |
| WO | 2006055288 | A2 | 5/2006 |
| WO | 2006060248 | A2 | 6/2006 |
| WO | 2006066023 | A2 | 6/2006 |
| WO | 2007038643 | A1 | 4/2007 |
| WO | 2007116386 | A1 | 10/2007 |
| WO | 2008115439 | A1 | 9/2008 |
| WO | 2008142580 | A2 | 11/2008 |
| WO | 2009027665 | A1 | 3/2009 |
| WO | 2009081180 | A1 | 7/2009 |
| WO | 2009118521 | A1 | 10/2009 |
| WO | 2010028044 | A1 | 3/2010 |
| WO | 2010091356 | A1 | 8/2010 |
| WO | 2011107972 | A1 | 9/2011 |

OTHER PUBLICATIONS

U.S. Appl. No. 11/248,082, filed Oct. 12, 2005 Final Office Action dated Mar. 28, 2012.
U.S. Appl. No. 11/248,082, filed Oct. 12, 2005 Non-Final Office Action dated Jul. 6, 2011.
U.S. Appl. No. 11/248,082, filed Oct. 12, 2005 Notice of Allowance dated Sep. 17, 2012.
U.S. Appl. No. 11/248,082, filed Oct. 12, 2005 Final Office Action dated Jun. 29, 2009.
U.S. Appl. No. 11/248,082, filed Oct. 12, 2005 Non-Final Office Action dated Dec. 21, 2010.
U.S. Appl. No. 11/248,082, filed Oct. 12, 2005 Non-Final Office Action dated Mar. 30, 2010.
U.S. Appl. No. 11/248,082, filed Oct. 12, 2005 Non-Final Office Action dated Oct. 30, 2008.
U.S. Appl. No. 11/248,082, filed Oct. 12, 2005 Notice of Allowance dated Jan. 12, 2010.
U.S. Appl. No. 11/248,082, filed Oct. 12, 2005 Notice of Allowance dated Oct. 15, 2010.
U.S. Appl. No. 11/248,082, filed Oct. 12, 2005 Restriction Requirement dated Jan. 10, 2008.
U.S. Appl. No. 11/535,245, filed Sep. 26, 2006 Non-Final Office Action dated Jul. 7, 2011.
U.S. Appl. No. 11/535,245, filed Sep. 26, 2006 Final Office Action dated Mar. 17, 2011.
U.S. Appl. No. 11/535,245, filed Sep. 26, 2006 Non-Final Office Action dated Oct. 12, 2010.
U.S. Appl. No. 12/188,955, filed Aug. 8, 2008 Final Office Action dated Jul. 13, 2012.
U.S. Appl. No. 12/188,955, filed Aug. 8, 2008 Final Office Action dated Nov. 6, 2013.
U.S. Appl. No. 12/188,955, filed Aug. 8, 2008 Non-Final Office Action dated Aug. 26, 2011.
U.S. Appl. No. 12/188,955, filed Aug. 8, 2008 Non-Final Office Action dated Jan. 11, 2012.
U.S. Appl. No. 12/188,955, filed Aug. 8, 2008 Non-Final Office Action dated Mar. 29, 2013.
U.S. Appl. No. 12/188,955, filed Aug. 8, 2008 Non-Final Office Action dated May 2, 2014.
U.S. Appl. No. 12/879,673, filed Sep. 10, 2010 Final Office Action dated Aug. 23, 2011.
U.S. Appl. No. 12/879,673, filed Sep. 10, 2010 Non-Final Office Action dated Feb. 1, 2011.
U.S. Appl. No. 13/469,849, filed May 11, 2012 Non-Final Office Action dated Aug. 1, 2012.
U.S. Appl. No. 13/469,849, filed May 11, 2012 Notice of Allowance dated Jun. 10, 2013.
U.S. Appl. No. 13/688,000, filed Nov. 28, 2012 Advisory Action dated Nov. 19, 2013.
U.S. Appl. No. 13/688,000, filed Nov. 28, 2012 Final Office Action dated Aug. 2, 2013.
U.S. Appl. No. 13/688,000, filed Nov. 28, 2012 Non-Final Office Action dated Apr. 23, 2013.
U.S. Appl. No. 13/688,000, filed Nov. 28, 2012 Non-Final Office Action dated Dec. 24, 2013.
U.S. Appl. No. 13/688,000, filed Nov. 28, 2012 Notice of Allowance dated Apr. 30, 2014.
Vargas, F.S. et al., "Comparison of Silver Nitrate and Tetracycline as Pleural Sclerosing Agents in Rabbits." Chest, vol. 108, No. 4, pp. 1080-1083, 1995.
"Experimental Plerueodesis in Rabbits Induced by Silver Nitrate or Talc," ASAP, vol. 199, No. 5, p. 1516, May 1, 2001.
"Management of Malignant Pleural Effusions." Am. J. Respir. Crit. Care Med., vol. 165, No. 5, pp. 1987-2001, 2000.
"Pleural Disease-Diagnosis and Management," The Practitioner, p. 412, May 1999.
"Pleurodesis," ASAP, vol. 118, No. 3, p. 577, Sep. 1, 2000.
AstraTech Healthcare, "Premium Wound Drainage Products," http://surgery.astratech.com/Main.aspx?Item=155788&navt=5&navl=82118&nava=81296, copyright 2010, printed Oct. 28, 2010.
Bard Access Systems, Inc., "Poly Per-Q-Cath PICC Catheter with Safety Excallibur Introducer," Instructions for Use, May 2003.
Bard, "Groshong NXT PICC Instructions for Use," Product Brochure, Nov. 2003.
Bellamy, R.F., "The Causes of Death in Conventional Land Warfare: Implications for Combat Casualty Care Research." Mil. Med., vol. 149, pp. 55-62, 1984.
Bilski, T.R., et al., "Battlefield Casualties Treated at Camp Rhino, Afghanistan: Lessons Learned", J. Trauma, vol. 54, No. 5, pp. 814-822, May 2003.
CA 2546434 filed Nov. 22, 2004 Office Action dated Dec. 15, 2010.
CA 2546434 filed Nov. 22, 2004 Office Action dated Oct. 3, 2011.
Campisi, P., et al., "Outpatient Treatment of Spontaneous Pneumothorax in a Community Hospital Using a Heimlich Flutter Valve: A Case Series." The Journal of Emergency Medicine, vol. 15, No. 1, pp. 115-119, 1997.
EP 04811627.1 filed Nov. 22, 2004 Office Action dated Aug. 17, 2012.
EP 04811627.1 filed Nov. 22, 2004 Office Action dated Feb. 11, 2014.
EP 04811627.1 filed Nov. 22, 2004 Office Action dated Feb. 23, 2011.
EP 04811627.1 filed Nov. 22, 2004 Office Action dated Jun. 5, 2014.
EP 04811627.1 filed Nov. 22, 2004 Supplementary European Search Report dated Oct. 22, 2004.
Groves Jr., "Operations in Urban Enviornments", Military Review, vol. 78, No. 4, Jul./Aug. 1998.
Heimlich, H.J., "Valve Drainage of the Pleural Cavity." Diseases of the Chest, vol. 53, No. 3, pp. 282-287, 1968.
Hewitt at al. "A Management Strategy for Malignancy-Induced Pleural Effusion: Long-term Thoracostomy Drainage." ONF, vol. 14, No. 5, 1987, pp. 17-22.

(56) References Cited

OTHER PUBLICATIONS

ICU-USA, "Wound Drainage," www.icu-usa.com/tour/procedures/drains.htm, copyright 1999-2004, printed Oct. 28, 2010.
ISO 10079-2 Medical Suction Equipment—Part 2: Manually Powered Suction Equipment, International Standard Organization 1999 (E).
Jaskille, et al., "A Portable Handpump is Effective in the Evacuation of Hemothorax in a Swine Model of Penetrating Chest Injury." The Journal of Trauma Injury, Infection, and Critical Care, Nov. 2003, pp. 864-868.
JP 06-541538 filed Nov. 22, 2004 Summarized Translation of Notice of Rejection (Office Action) dated Jun. 23, 2009.
JP 06-541538 filed Nov. 22, 2004 Summarized Translation of Notice of Rejection (Office Action) dated Mar. 2, 2010.
JP 06-541538 filed Nov. 22, 2004 Summarized Translation of Notice of Rejection (Office Action) dated Oct. 1, 2010.
Light, R.W. et al., "A Single Intrapleural Injection of Transforming Growth Factor-Beta(2) Produces an Excellent Pleurodesis in Rabbits." Am. J. Respir. Crit. Care Med., vol. 162, No. 1, pp. 98-104, 2000.
Light, R.W. et al., "Talc Slurry is an Effective Pleural Sclerosant in Rabbits." Chest, vol. 106, No. 6, pp. 1702-1706, 1995.
Lodi, R., et al., "A New Portable Chest Drainage Device." Ann. Thorac. Surg., vol. 69, pp. 998-1000, 2000.
Mabry, R.L., et al., "United States Army Rangers in Somalia: An Analysis of Combat Casualties on an Urban Battlefield", J. Trauma. vol. 49, No. 3, pp. 515-529, Sep. 2000.
Medcomp Ash II Split Cath™ "Features and Benefits" product brochure. Oct. 1999.
Medcompare, "Drains with Reservoirs," General Surgery Product Matrix, Medompare.com/matrix/1885/Drains-with-Reservoirs.html, copyright 2003-2010, printed Oct. 28, 2010.
Milton, Jr., T.R., "Urban Operations: Future War", Military Review, vol. 74, Issue 2, Feb. 1994.
Montes, J.F. et al., "Influence of Talc Dos on Extrapleural Talc Dissemination after Talc Pleurodesis." Am. J. Respir. Crit. Care Med., vol. 168, No. 3, pp. 348-355, 2003.
Ohm, et al. "Use of Indwelling Pleural Catheter Comparaed with Thorascopic Talc Pleurodesis in the Management of Malignant Pleural Effusions." Division of Thoracic Surgery and Department of Surgery, William Beaumont Hospital, The American Surgeon Mar. 2003, vol. 69, pp. 198-202.
PCT/US2004/038937 filed Nov. 11, 2004 Preliminary Report on Patentability dated Jul. 5, 2005.
PCT/US2004/038937 filed Nov. 22, 2004 Search Report dated Jul. 5, 2005.
PCT/US2006/037766 filed Sep. 26, 2006 Preliminary Report on Patentability dated Mar. 26, 2008.
PCT/US2006/037766 filed Sep. 26, 2006 Search Report dated Jan. 25, 2007.
PCT/US2006/037766 filed Sep. 26, 2006 Written Opinion dated Mar. 26, 2008.
Pope, A., et al., "Fluid Resuscitation: State of the Science for Treating Combat Casualties and Civilian Injuries." National Academy Press, 1999.
Schweitzer, E.F. et al., "Use of Heimlich Valve in Compact Autotransfusion Device." The Journal of Trauma, vol. 27, No. 5, pp. 537-542, 1987.
Tremblay, A. et al., "Single-Center Experience with 250 Tunnelled Pleural Catheter Insertions for Malignant Pleural Effusion." Chest, vol. 129, No. 2, pp. 362-368, 2006.
U.S. Appl. No. 10/595,450, filed Jun. 21, 2007, titled Portable Hand Pump for Evacuation of Fluids, listing Hasan B. Alam, Peter Rhee and Emily Rhee as inventors.
U.S. Appl. No. 10/595,450, filed Jun. 21, 2007 Final Office Action dated Jul. 17, 2009.
U.S. Appl. No. 10/595,450, filed Jun. 21, 2007 Final Office Action dated Oct. 1, 2010.
U.S. Appl. No. 10/595,450, filed Jun. 21, 2007 Non-Final Office Action dated Apr. 9, 2010.
U.S. Appl. No. 10/595,450, filed Jun. 21, 2007 Non-Final Office Action dated Jun. 12, 2013.
U.S. Appl. No. 10/595,450, filed Jun. 21, 2007 Non-Final Office Action dated Oct. 30, 2008.

\* cited by examiner

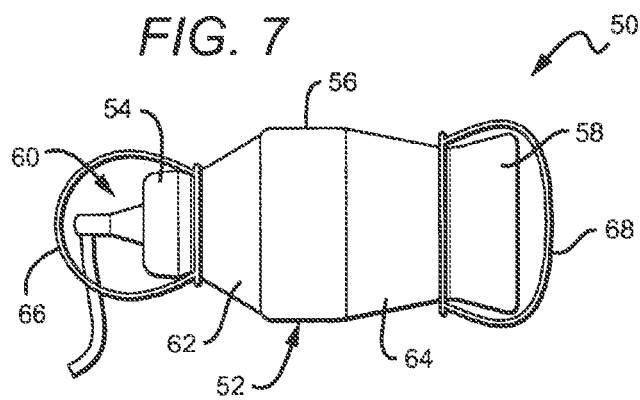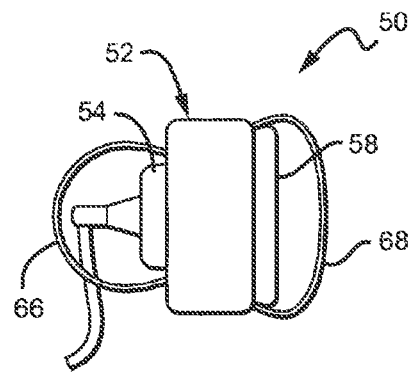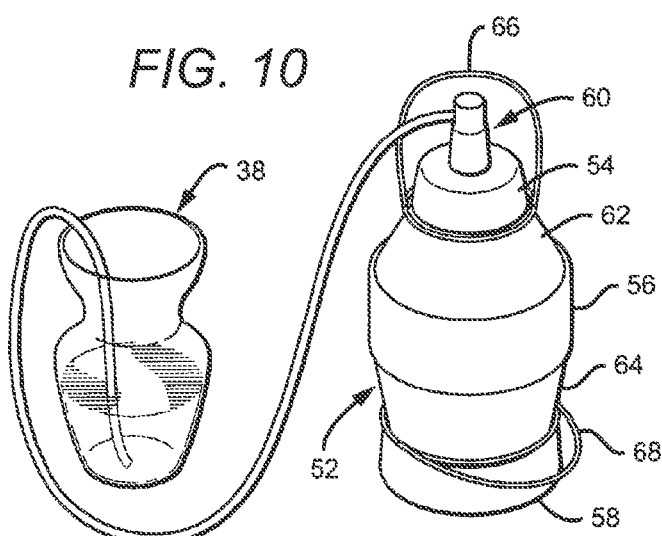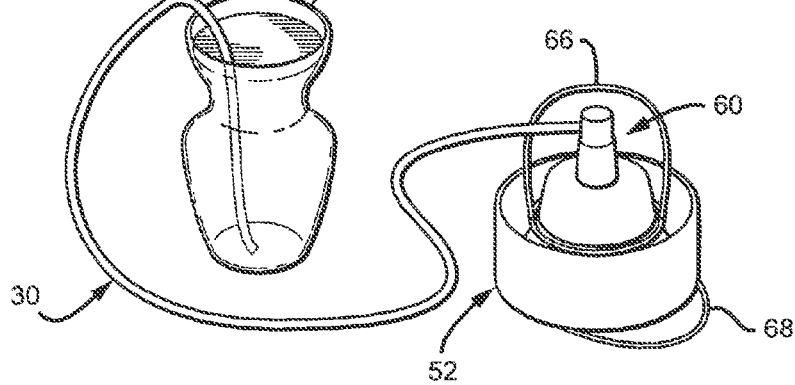

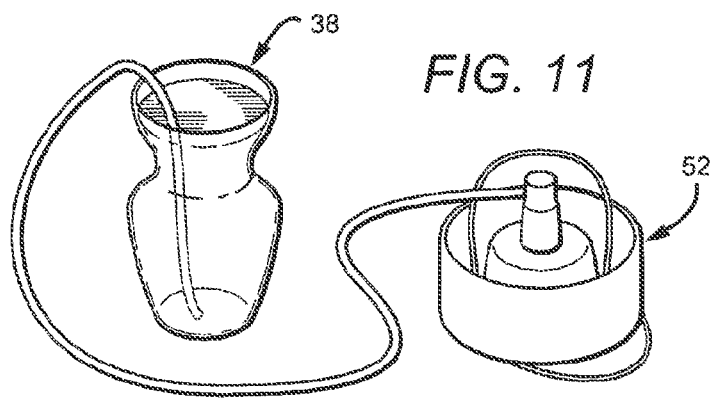
FIG. 11
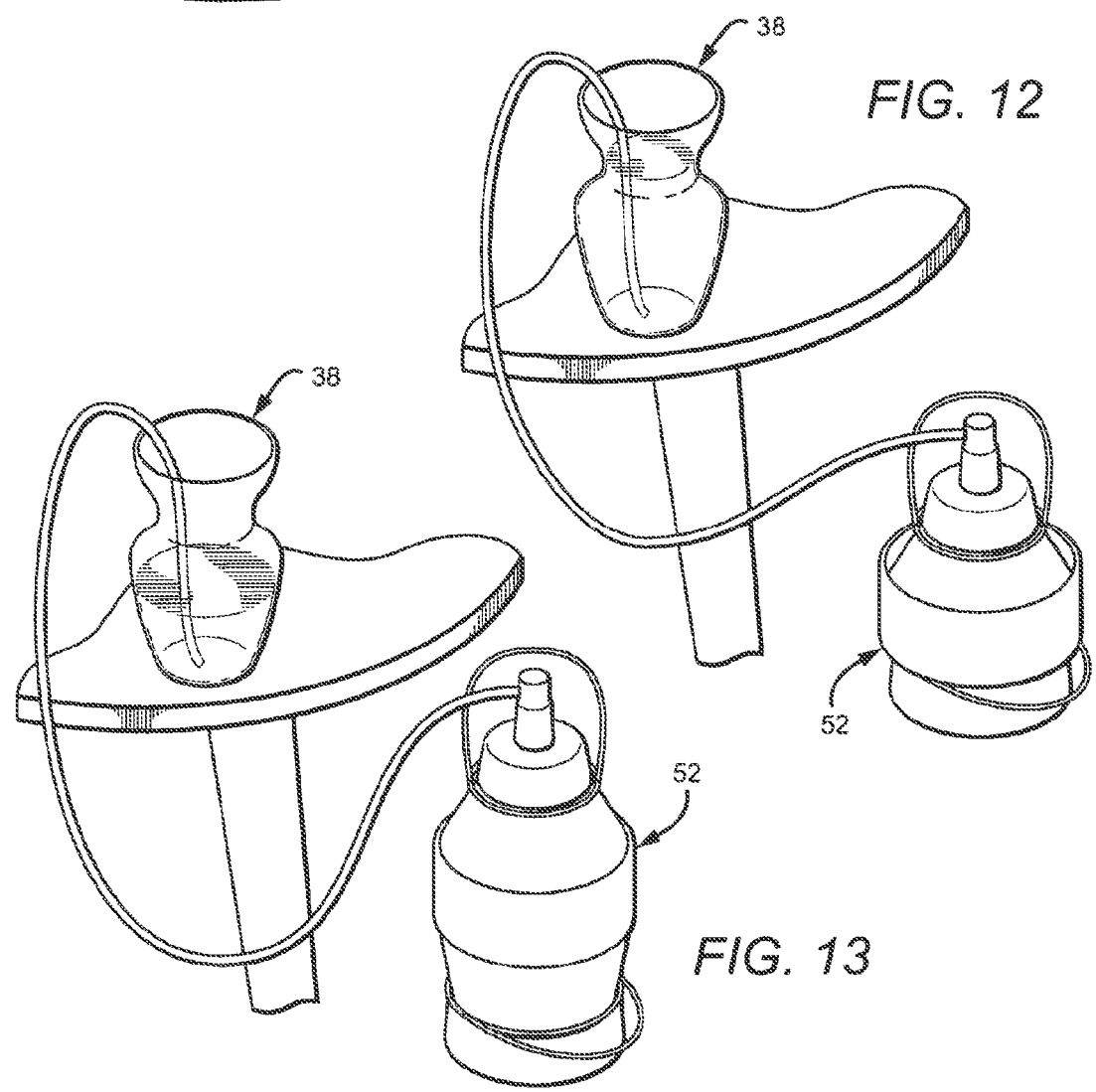
FIG. 12
FIG. 13

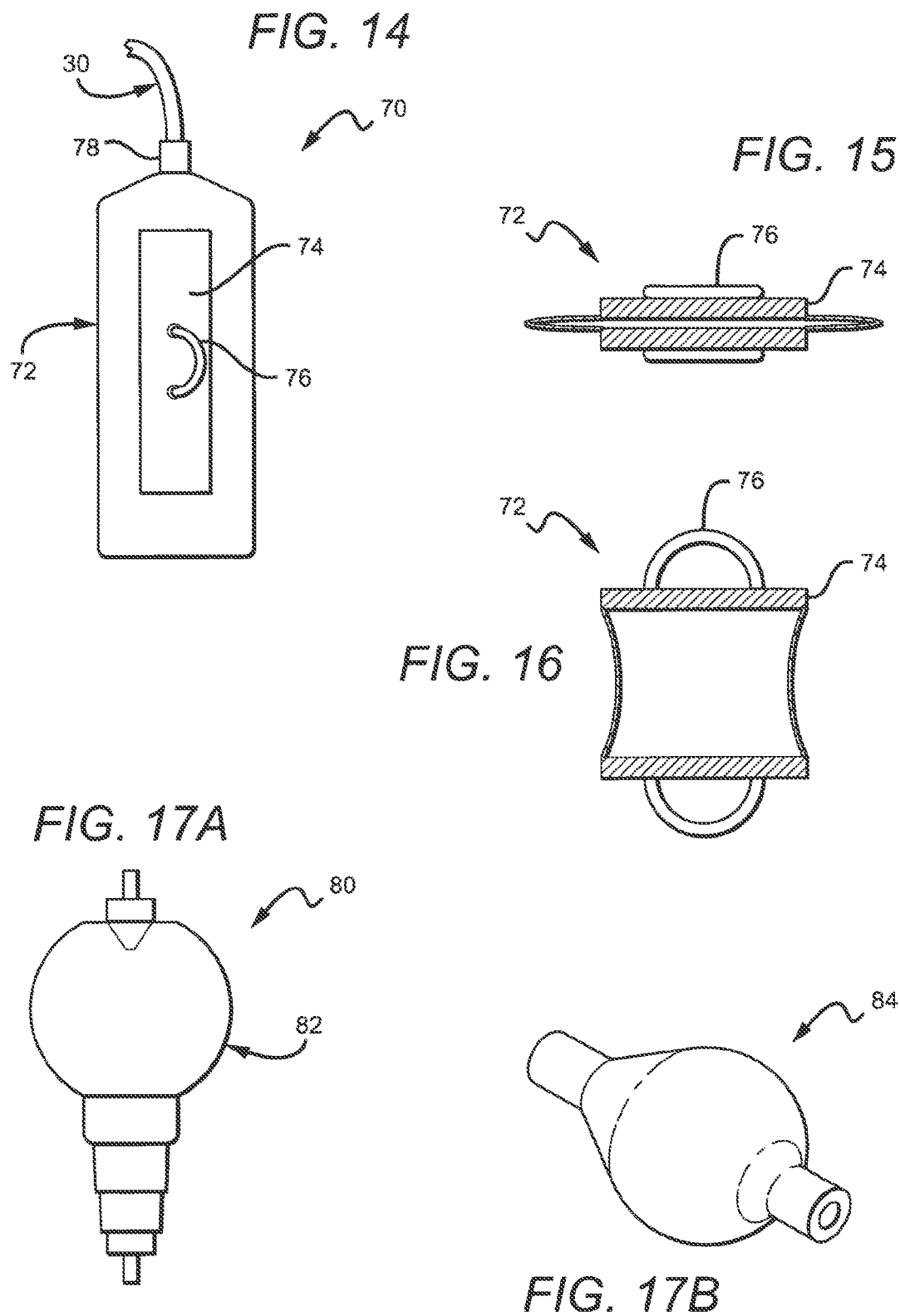

CORPOREAL DRAINAGE SYSTEM

PRIORITY

This application is a division of U.S. patent application Ser. No. 13/688,000, filed Nov. 28, 2012, now U.S. Pat. No. 8,814,839, which is a division of U.S. patent application Ser. No. 11/248,082, filed Oct. 12, 2005, now U.S. Pat. No. 8,337,475, which claims the benefit under 35 U.S.C. §119(e) of U.S. Provisional Application No. 60/617,758, filed Oct. 12, 2004, each of which is expressly incorporated by reference as if fully set forth herein.

BACKGROUND OF THE INVENTION

Fluid accumulation due to sickness or trauma may develop in areas within a mammalian body not designed to accommodate such accumulation. One particular area prone to abnormal accumulation is between sheets of tissue covering the outside of the lung and lining the chest cavity, known as the pleural space. While a normal functioning pleural space contains approximately 5-20 mL of fluid, fluid turnover occurs on an hourly basis such that approximately 5-10 L of fluid passes through the pleural space every day. Thus, any disruption in fluid turnover may result in over-accumulation of fluid in the pleural space, known as pleural effusion. The symptoms of pleural effusion include dyspnea, tachycardia, cough, breathing difficulty and chest pain as the lungs are prevented from fully expanding upon breathing. Pleural effusion is a condition secondary to trauma, cancer, nephrotic syndrome, kidney disease, pancreatitis, congestive heart failure and cirrhosis, and as such, patients affected with pleural effusion will usually die within three months of onset. Consequently, treatment of pleural effusion is generally provided for patient quality of life in his/her final days.

There are numerous methods to treat pleural effusion and/or other unwanted fluid accumulation in a mammalian body. Fluid drainage procedures, such as thoracentesis, may be used to provide patient relief. Thoracentesis involves the introduction of a needled catheter into the pleural space through an incision in the chest cavity, after which fluid is drawn out using a syringe or a vacuum source. Drawbacks with this procedure, however, include the fact that the needle may inadvertently puncture a lung, leading to aggravation of the problem, and the fact that fluid readily re-accumulates in the pleural space after the procedure is performed such that it may become necessary for a patient to undergo the procedure every few days. Pleurodesis is a procedure in which fluid is prevented from accumulating due to the sealing of the space between pleura with either sterile talc or an antibiotic, after first draining the existing fluid. Another method to treat pleural effusion is to surgically implant a chest tube or catheter such that fluid accumulation can constantly or periodically be removed without invasive surgery. The implanted catheter may be connected to an external catheter or drainage tube by a one-way valve mechanism, which permits fluid drainage through the use of a negative pressure source, such as a vacuum. One example of such a catheter system is described in U.S. Pat. No. 5,484,401 to Rodriguez et al., which is expressly incorporated by reference as if fully set forth herein.

While catheter-based systems have been described in the prior art, and indeed are being utilized by patients in the US, significant drawbacks exist. For example, although effective and clinically acceptable, existing catheter-based systems suffer from one or more of the following deficiencies: 1) the catheter/drainage tube connection is not secure and can be easily pulled apart (while not life threatening, accidental disconnection will cause loss of vacuum pressure mandating set-up with a new system; also, such disconnects can be the cause of pleural or peritoneal infection); 2) the clamp supplied on the drainage tube is difficult to use and is not an effective means of controlling fluid flow; 3) the system is useless in the event of an accidental loss of vacuum (effective safety mechanisms designed to prevent such accidental or premature loss of vacuum are missing); 4) the clamp sealing the vacuum chamber (which must be removed in order to activate drainage) is difficult for older patients and care givers to detach; 5) the collection chambers provided with the drainage systems (typically 500 mL) are not adequately sized for peritoneal drainage where fluid collection volumes can reach 2000 mL.

Thus, there is a need for an improved system for corporeal drainage, which will provide beneficial aspects, including those that will facilitate the use thereof regardless of patient location or condition.

BRIEF DESCRIPTION OF THE DRAWINGS

FIG. 7 is a side plan view of another embodiment of a corporeal drainage system, showing a fluid receptacle in the form of a bottle in an expanded state.

FIG. 8 is a side plan view of the corporeal drainage system of FIG. 7, showing the bottle in a collapsed state.

FIG. 9 is a perspective view of the corporeal drainage system of FIG. 8, showing a distal end of a connection tube inserted into a container holding an amount of fluid to simulate the drainage of a bodily cavity.

FIG. 10 is a perspective view of the corporeal drainage system of FIG. 9, following expansion of the bottle and transfer of the fluid from the container into the bottle.

FIGS. 11-13 are perspective views of the corporeal drainage system of FIGS. 9-10, illustrating a passive siphoning process.

FIG. 14 is a side plan view of a fluid receptacle for use with a corporeal drainage system, in which the fluid receptacle also is configured to initiate a negative pressure in the system.

FIG. 15 is a longitudinal cross-sectional view of the fluid receptacle of FIG. 14 in a collapsed state.

FIG. 16 is a longitudinal cross-sectional view of the fluid receptacle of FIG. 14 in an expanded state.

FIGS. 17A-C illustrate a hand pump for use with a corporeal drainage system, the pumps in the figures all having a bulbous configuration.

BRIEF SUMMARY OF THE INVENTION

Figure 1:
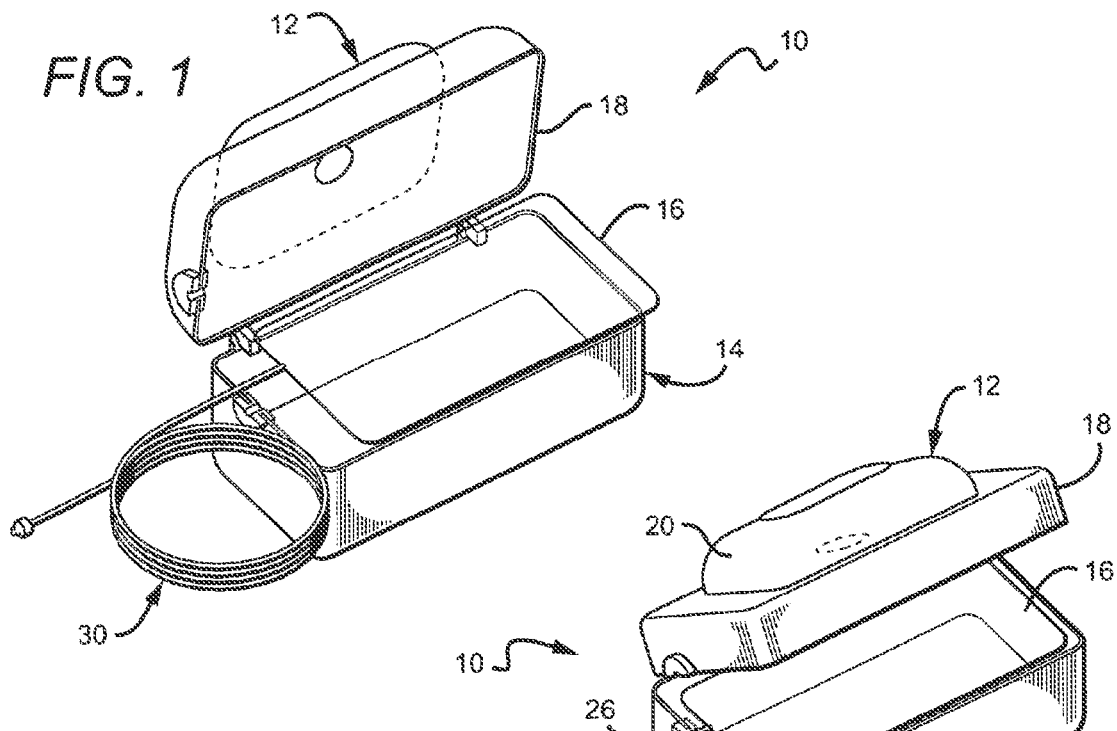
FIG. 1 is a perspective view of a corporeal drainage system, showing a container in an open position for positioning of a disposable fluid collection bag.

Accordingly, a corporeal drainage system is described herein that provides beneficial aspects to a target user. In one aspect of the invention, a corporeal drainage system utilizes an inline pump that connects to both the implanted catheter and drainage tube via unidirectional check valves. In another aspect, an inline drip chamber is provided for a corporeal drainage system to monitoring drainage from a bodily cavity. In one embodiment, the inline pump made of a transparent material such that it serves the dual purpose of providing both an inline pump and a drip chamber.

In another aspect of the invention, a corporeal drainage system is configured for use as a passive siphoning system, in which a negative pressure is created following initial activation, in order to alleviate work required by a user in operating the system. In one embodiment, following initial activation (e.g., pump is primed, collapsible container is initially expanded from a collapsed state, etc.), the system is positioned at a level below the reservoir or cavity to be drained to create a siphon system where the weight of the fluid in the tubing acts to drag fluid out of the elevated reservoir. In another aspect of the invention, a corporeal drainage system includes a semi-reusable collection system having a multiple use outer rigid container with single use disposable inner plastic collection bag liners that has the capacity to reactivate the required vacuum for use. In still another aspect of the invention, a corporeal drainage system is configured as a single use, low cost collection system with a pre-loaded force, in which the fluid receptacle also acts as a catalyst for producing a negative pressure in the system. In one embodiment the collection system includes a bottle that is locked in a collapsed state for shipping and storing and can be activated by unlocking. In another embodiment, the collection system includes a disposable bag that can be primed or activated to produce a negative pressure, while also serving as a fluid receptacle.

In another aspect of the invention, a corporeal drainage system is provided such that an implanted catheter can be securely connected to an external fluid flow conduit with minimal effort through use of a convenient connection system. In one embodiment, the connection system includes a catheter connector that can be connected to a drainage line connector.

In one embodiment, a corporeal drainage system includes an implantable catheter, a connection tube, a connection system, including a catheter connector attached to a proximal end of the catheter and a drainage line connector attached to a distal end of the connection tube, and a pump, including a first unidirectional check valve and a second unidirectional check valve, wherein the first unidirectional check valve is positioned at one end of the pump to connect the pump to the fluid receptacle and the second unidirectional check valve is positioned at an opposite end of the pump to connect the pump to the connection tube.

In another embodiment, a corporeal drainage system includes a catheter including a catheter connector at a proximal end thereof, a connection tube including a drainage line connector at a distal end thereof, the drainage line connector and catheter connector being configured for sealing attachment to one another, and a disposable fluid receptacle in fluid communication with the connection tube, the fluid receptacle being configured to create a negative pressure within the system upon activation thereof.

A method of draining fluid from a bodily cavity using a corporeal drainage system having a fluid receptacle includes attaching a connection tube to the proximal end of an implanted catheter, initiating a negative pressure in the system such that fluid flows from the bodily cavity in a direction toward the proximal end of the catheter, and placing the fluid receptacle at a level below the bodily cavity.

These and other objectives, embodiments, features and advantages of the present invention will become more apparent to those skilled in the art when taken with reference to the following more detailed description of the invention.

DETAILED DESCRIPTION OF THE INVENTION

The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The embodiments described herein are directed to a corporeal drainage system designed to effectively provide a user the ability to drain fluid from their body in a non-clinical setting with a minimum amount of effort. The embodiments of the invention generally contain a connection tube having a proximal end that is either detachably or permanently connected to a pump or container and a distal end that is fashioned with a connector device that permits quick, easy and secure attachment to a device or mechanism inserted within a bodily cavity, including, for example, an indwelling device such as an implanted catheter or port. The connector device may be a standard luer connector or other like connectors as known to one skilled in the art. For example, if an implanted catheter has at its proximal end a female needleless injection port, the connection tube can have at its distal end a male luer connector. Particular connection systems to sealingly connect an implanted catheter to a fluid flow conduit in a corporeal drainage system are disclosed in commonly owned U.S. Provisional Application No. 60/720,443, filed Sep. 26, 2005, entitled "Catheter Connection System," the complete contents of which are expressly incorporated by reference as if fully set forth herein.

The connection tube may be made of polyurethane or other material known to one skilled in the art suitable for a bodily fluid conduit. The connection tube should be of sufficient length to accommodate all users, such that the container may be placed on the ground or at a location beneath the cavity to be drained without undue discomfort. If the system is configured with a connection tube that is detachable from the container, different lengths can be provided by the treating clinician depending on height of the user and/or other parameters, such as likely location for the draining operation, length of the catheter extending outside of the patient's body, etc. Currently, the standard contemplated length of the connection tube is in the range of approximately 3 ft to 5 ft. The implanted catheter may be any standard medical catheter suitable for insertion into a bodily cavity, having at its proximal end a connector that attachably cooperates with the connector device attached to the connection tube (e.g., male or female luer connector). For example, suitable catheters include peritoneal catheters, thoracic drainage catheters, etc. Moreover, in the embodiments of the invention, a fluid receptacle, which may take the form, for example, of a container, disposable bottle and/or disposable bag can hold approximately 1 L of fluid, although certainly a wide range of volume capability is contemplated for the fluid receptacles of the present invention (e.g., in the range of approximately 0.5 L to 5 L).

Figure 2:
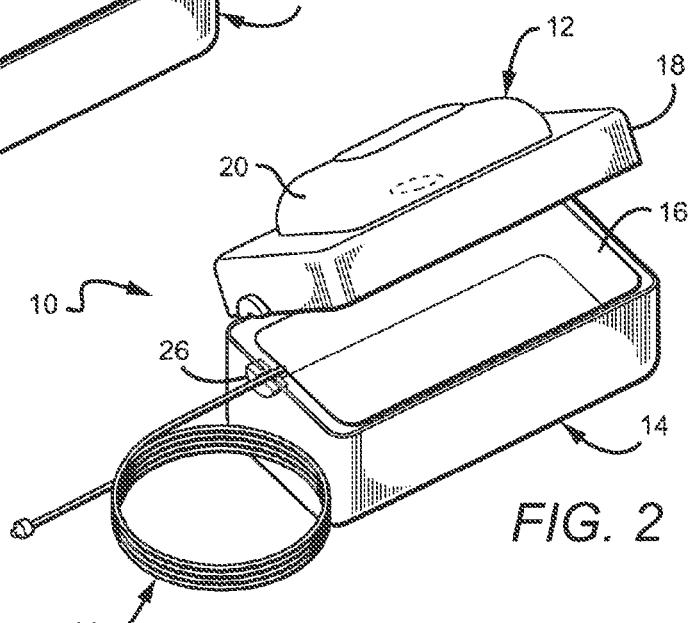
FIG. 2 is a perspective view of the corporeal drainage system of FIG. 1, showing the container in a semi-closed position.
Figure 3:
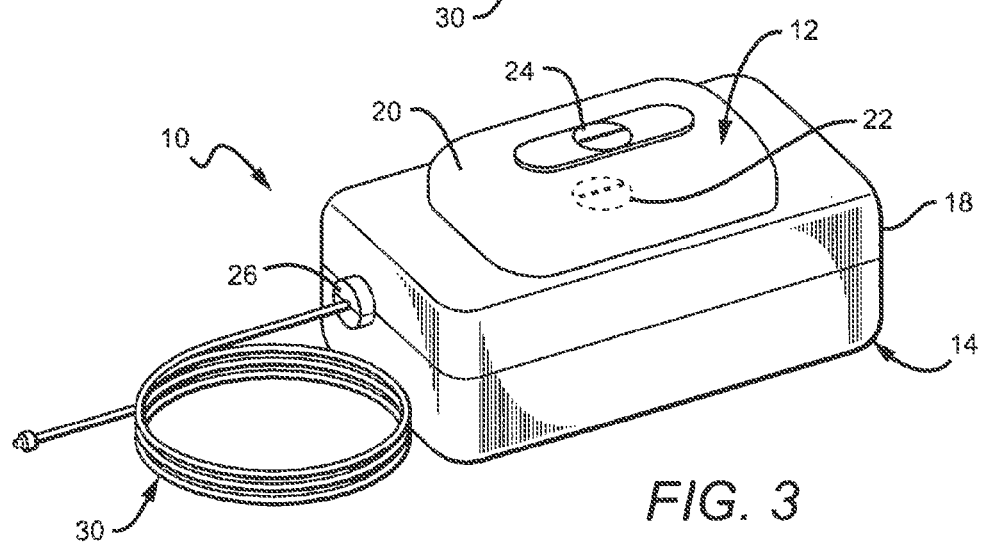
FIG. 3 is a perspective view of the corporeal drainage system of FIG. 1, showing the container in a closed position.

Referring now to FIGS. 1-3, a corporeal drainage system 10 includes a vacuum pump 12, a vacuum box/container 14, a drainage bag 16 and a connection tube 30. The connection tube 30 is as described above. The vacuum pump 12 may include a flexible membrane 20 and a pair of one-way check valves 22 (FIG. 3) and can be fashioned in various shapes and sizes. The one-way check valves 22, 24, may be any type of unidirectional flow valve as is well-known to one skilled in the art. The vacuum pump 12 is operatively associated with the container via a first one-way check valve 22, which permits evacuation of air while maintaining a vacuum as it is created within the system 10. In particular, the first one-way check valve 22, permitting movement of air from the container, connects the vacuum pump 12 to the container 14. A second one-way check valve 24, positioned on the vacuum pump 12, permits release of air from the pump 12. Thus, creation of a negative pressure in the system 10 includes first activating the pump 12 through compression thereof (e.g., pressing downward on the flexible membrane 20), which evacuates the air inside the vacuum pump 12 through the second check valve 24 positioned on the pump 12, and second releasing the pump 12 (e.g., removing the applied pressure from the flexible membrane 20), which permits expansion thereof by pulling air from the container 14 through the first check valve 22.

The vacuum pressure provided to the system 10 is dependent on a number of factors, such as, for example, the number of times the pump 12 is activated (e.g., the number of times pressure is applied to the flexible membrane 20 and subsequently released), which can be varied based on the type of material used and the surface area of the pump 12 (rebound force of the pump (F)/surface area (A)=pressure (P)). Literature suggests that a negative pressure of approximately 30 mm Hg is the maximum that most bodily cavities in mammals are capable of withstanding. Thus, with such a relatively small amount of pressure demanded for the system, the volume of the pump and the material choice for the pump, including wall thickness and durometer, must be carefully considered so that a balance is struck between the number of pumps needed and amount of force necessary for a single activation of the pump. Such selection of wall thickness and durometer will also permit one to control the negative pressure placed into the system, which can be limited to provide a safety function (i.e., the amount of negative pressure possible can be limited by material selection such that even if the maximum amount was achieved by the user, said amount would not exceed the maximum permissible for the bodily cavity to be drained). Given the fact that system 10, and other systems described herein, will likely be used by patients with diminished strength and energy, these considerations can play an important role in the design of the system. In an exemplary embodiment, the flexible membrane 20 of pump 12 is made of 55 Shore A polyvinylchloride with a wall thickness in the range of approximately 0.05 in to approximately 0.5 in.

In order to maintain a consistent flow of fluid from the bodily cavity in prior art systems, the pump needs to be activated at least intermittently by the user. As previously mentioned, however, the target user may be unable or unwilling to do so. Thus, an advantage of the system described herein is that it is designed with the ability to act as a siphon after initial activation. Specifically, once the user has activated the pump a few times (e.g., in the system 10 described above, when the user has collapsed the flexible membrane 20 and subsequently allowed air from the system to re-expand it two or more times), the user may then place the container (e.g., container 14) on the ground (or any location below the body cavity from which drainage is taking place), which effectively creates a passive siphon system that utilizes the weight of the fluid within the catheter and/or connection tube 30 to pull fluid out of the bodily cavity (elevated reservoir). This ability to create a passive system requires only minimal effort from the user, which allows the system to be used in a non-clinical setting by a wide range of users, regardless of physical condition.

The vacuum box/container 14, while illustrated in a rectangular box form, may take on virtually any shape. The container 14 may include a lid 18 that is hinged to a body, as shown in FIGS. 1-3, in order to simplify the removal and installation of a disposable bag 16, although many configurations without a hinged lid 18 are also possible and within the scope of the invention as would be apparent to one skilled in the art. Due to the configuration of the system 10 that includes a disposable bag 16, the system can be used numerous times. An aperture configured for passage of the connection tube 30 is positioned on a side of the container, having associated with it a grommet 26 made of a material, such as silicone rubber, to provide a sealing function for the aperture. In one embodiment, the container also has a gasket positioned around the lid or disposable bag opening such that when said lid or opening is closed, an enhanced seal is provided. The connection tube 30 is detachable from the container 14 in one embodiment to facilitate cleaning of the container 14 (see FIG. 1). In other embodiments, the connection tube 30 is permanently connected to the container 14. The container 14 may be made of a rigid plastic material, although many other rigid materials are also suitable, such as, for example, polycarbonate, high density polypropylene, nylon, Lexan®, stainless steel, etc. In the event that the system is designed to be reusable, such as the embodiment shown in FIGS. 1-3, the material choice should be one that may be readily cleaned (e.g., dishwasher safe).

Figure 4:
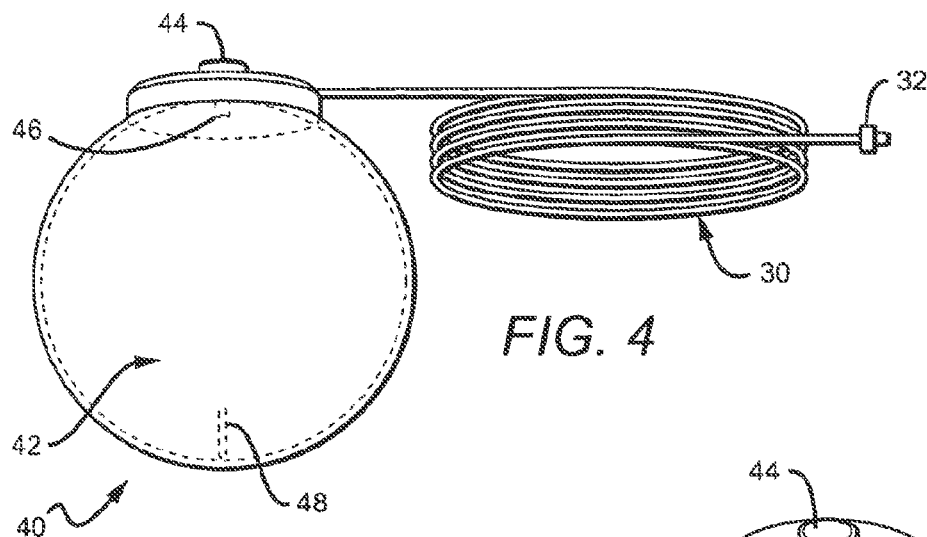
FIG. 4 is a bottom perspective view of another embodiment of a corporeal drainage system, showing in phantom a latch tab and latch clasp. The fluid receptacle is shown in an expanded state.
Figure 5:
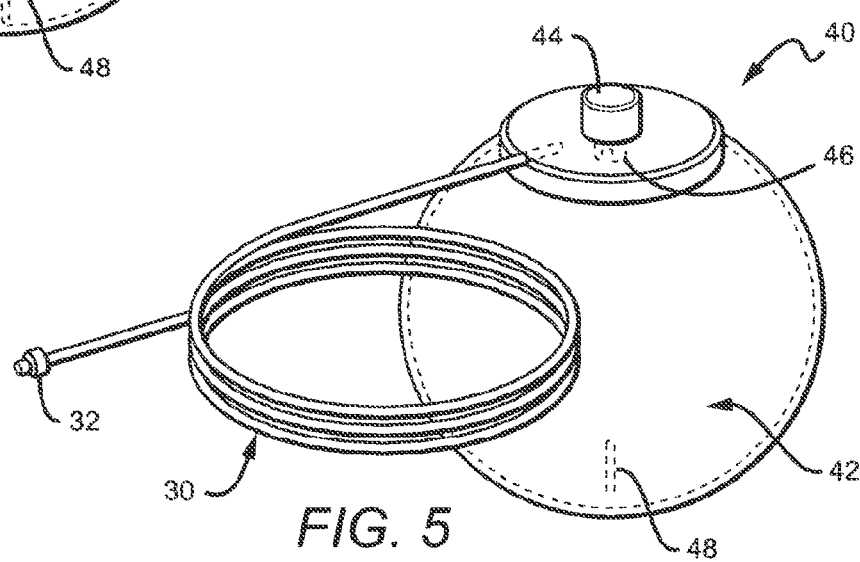
FIG. 5 is a top perspective view of the corporeal drainage system of FIG. 4.
Figure 6:
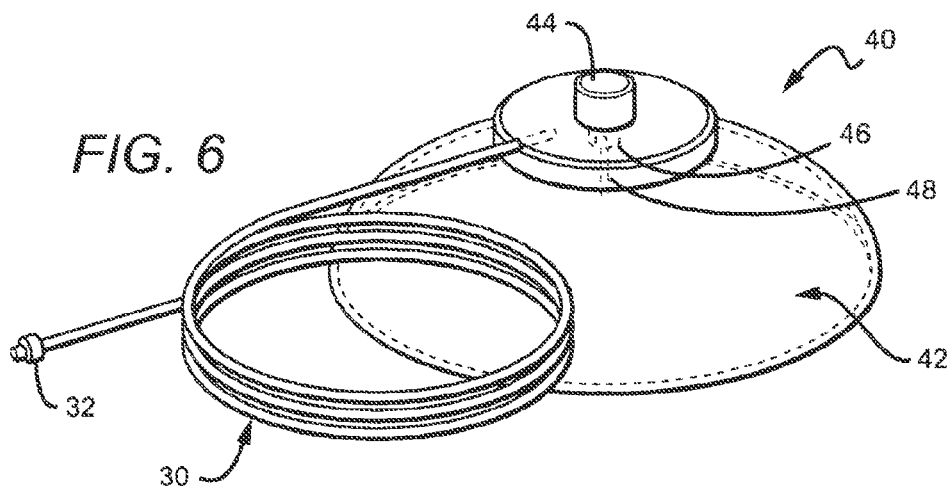
FIG. 6 is a top perspective view of the corporeal drainage system of FIG. 4, shown in a collapsed state in which the latch tab is connected to the latch clasp.

FIGS. 4-6 illustrate another embodiment of a corporeal drainage system 40, including a disposable bottle 42 made of a material, such as a clear rubber or other elastomer, that serves the dual purpose of acting both as a fluid receptacle and a catalyst or initiator for producing a negative pressure in the system. The term "bottle" as used herein means any type of container that can be filled with fluid, at least a portion of which can be collapsed, at least in part, to evacuate air therefrom. The bottle 42 in FIGS. 4-6 is in the form of a ball, having an activation knob 44 on the exterior of one end and a latch tab 48 on the interior of an opposite end. The activation knob 44 is operatively connected to a latch clasp 46 positioned adjacent the knob on the interior of the bottle 42. The bottle 42 may be molded in an open configuration and then collapsed for shipping. Upon collapse of the bottle 42, the latch clasp 46 and the latch tab 48 connect to lock the bottle in a collapsed condition, pending activation (e.g., by pressing, turning, etc.) of the activation knob 44. In this collapsed state for shipping, the bottle has a pre-loaded force so that unlocking of the latch clasp from the latch tab results in activation of the system with minimal physical effort required of the user.

When the user is ready to initiate drainage of a bodily cavity, the connection tube 30 is attached to an implanted catheter via the connector 32 (e.g., luer member), or connection system as described in commonly owned U.S. Provisional Application No. 60/720,443, and the activation knob 44 is activated, unlatching the latch clasp 46 from the latch tab 48 and permitting the bottle 42 to expand, pulling fluid from the bodily cavity in the process. In order to generate sufficient force to draw the fluid out of the bodily cavity, the wall thickness of the bottle 42 must be carefully considered. In an exemplary embodiment, the bottle 42 is approximately the size of a softball, is made of an elastomeric material, and has a wall thickness in the range of approximately 0.05 in. to approximately 0.5 in. In this embodiment, the material of the bottle 42 is disposable, such that once the fluid has been extracted from the bodily cavity, the bottle 42 can be disposed of; each use requiring a new bottle. In other embodiments, the bottle 42 may include an opening such that a disposable bag or other fluid-holding container can be inserted and removed therefrom.

FIGS. 7-13 illustrate another embodiment of a corporeal drainage system, including a bottle. In this embodiment, the bottle 52 of system 50 includes rigid sides, including a top section 54, middle section 56 and base section 58, and flexible connecting walls, including first connecting wall 62 positioned between the top section 54 and middle section 56 and second connecting wall 64 positioned between middle section 56 and base section 58. The connecting walls 62, 64 are configured to collapse within the rigid sides 54, 56, 58 upon activation of the system 50. The top section 54 has a connection member 60, which is configured to be removably attached to connection tube 30. Both top section 54 and base section 58 have respective pull tabs 66 and 68 attached thereto, the pull tabs functioning to facilitate the expansion of the bottle 52, following collapse, upon initiation of a drainage procedure. FIG. 7 illustrates the bottle 52 prior to collapse, while FIG. 8 illustrates the bottle 52 following collapse. As is apparent from FIG. 8, in this embodiment, the connecting walls 62, 64 collapse substantially within the rigid sides 54, 56, 58 to provide a small profile for storage and shipping.

FIG. 9 shows bottle 52 in its collapsed form, as shipped and stored, with the connection tube 30 attached to the connection member 60 at one end with an opposite end inserted into a container 38 with an amount of fluid therein, which exemplifies the draining of a bodily cavity. As discussed, the system 50 is activated by pulling on the pull tabs 66, 68 to expand the bottle 52, as illustrated in FIG. 10. The expansion of the bottle 52 results in the fluid from the container 38 being suctioned into the bottle 52. When the bottle is fully expanded, as shown in FIG. 10, a suitable amount of suction has been imparted to the system 50 such that a majority of fluid from the container 38 is transferred to the bottle 52. The amount of force required to expand the bottle 52 to an expanded state is dependent on a variety of factors, including the material of the bottle, as discussed above. The amount of expansion of bottle 52 necessary to drain a particular bodily cavity is variable and also depends on a number of factors, including the amount of fluid to be drained. FIGS. 9-10 illustrate an active siphoning process, in which the siphoning or transfer of fluid from the container 38 to the bottle 52 is directly attributable to the expansion of the bottle 52 (i.e., the pulling force applied to the pull tabs 66, 68 as they are pulled in opposite directions). However, the transfer of fluid from container 38 to bottle 52 can also be accomplished through a passive siphoning process, requiring much less force. This alternative method of siphoning, for which system 50 is also designed, is explained in more detail with reference to FIGS. 11-13.

Through experimentation, it was noted that a pulling force of approximately 20 lbs was required to fully expand bottle 52, in order to drain fluid from a bodily cavity. Because such a force requirement may be prohibitive to some users, another method of creating a vacuum was explored. It was discovered that an initial pulling force, significantly less than the 20 lbs necessary to fully expand the bottle 52, acted to begin the fluid flow through the catheter and connection tube. FIG. 11 shows the bottle 52 in its collapsed state, positioned at the same level as the container 38 with a level of fluid therein. In the experiment, once fluid began to enter the bottle 52, the bottle 52 was dropped to the floor or at a level below the container 38. FIG. 12 shows the bottle 52 after an initial pulling force, less than 20 lbs, has been applied to the system 50 (i.e., the pull tabs 66, 68 have been pulled in opposite directions), the bottle 52 being positioned at a level below the container 38. The action of providing an initial pulling force coupled with the action of dropping the bottle below the container generated a siphon within the system 50, pulling fluid from the container 38 and eventually filling the bottle 52. As the transfer of fluid from the container 38 to the bottle 52 takes place, the bottle 52 continues to expand until fully expanded as illustrated in FIG. 13.

Thus, the experiment showed that a reduced pulling force, less than the force required to fully expand bottle 52, could be utilized with similar results, thereby overcoming the potential problem of requiring a user to provide a larger pulling force than could be achieved by the user. It should be noted that the amount of negative head pressure (i.e., the level or distance of a bottle or container positioned below the drainage reservoir (bodily cavity)) controls the fill rate of the bottle and amount of suction acting on the drainage catheter. Therefore, as the bottle expands and increases in weight, fluid flow rate increases. As such, in one embodiment, a bottle, such as bottle 52, is hung or otherwise suspended with a weight attached to the base thereof to increase flow rate. In another embodiment, a bottle is made of a clear material so that, in addition to the audible flow indication, a visual flow indication would be provided to the user.

FIGS. 14-16 illustrate another embodiment of a corporeal drainage system. In this embodiment, system 70 includes a disposable bag 72 without an associated container, the disposable bag 72 being made of a disposable material so that it serves as a fluid receptacle. The disposable bag 72 is also configured such that it can be directly manipulated (similar to the bottle 52 of FIGS. 7-13) to produce a negative pressure for the purposes of fluid drainage from a bodily cavity. The disposable bag 72 is fashioned with rigid members 74 attached to opposing sides of the bag 72, the rigid members 74 having pull tabs 76 connected thereto. The rigid surface area of the rigid members 74 compared to the flexible surface area of the flexible portion of bag 72 is calculated such that a sufficient amount of vacuum can be generated by pulling the rigid members 74 in opposite directions (thereby expanding the bag). FIG. 14 is a perspective view of the system 70, showing one side of the bag 72 with rigid member 74 and pull tab 76, and a connection member 78 attached to one end of the bag 72, configured for releasable attachment to connection tube 30. FIG. 15 illustrates a lengthwise cross-sectional view of the disposable bag 72 in a collapsed state prior to initiating drainage (i.e., prior to imparting a negative pressure to the system 70). FIG. 16 illustrates a lengthwise cross-sectional view of the disposable bag 72 in an expanded state, following a pulling force being applied to the pull tabs 76 (i.e., the pull tabs 76 are pulled in opposite directions). As with the system 50 described above, system 70 can be operated as both active (i.e., utilizing only a pulling force to expand the bag 72) and passive (i.e., providing an initial pulling force to begin fluid flow and subsequently positioning the bag 72 below the level of fluid to be drained).

Figure 17C:
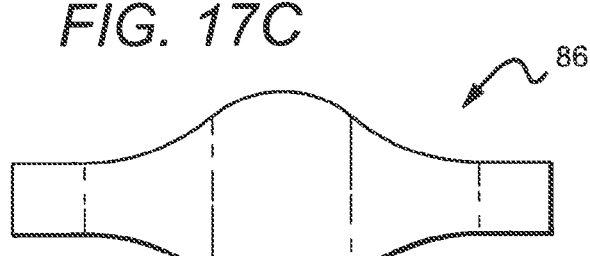
Figure 18:
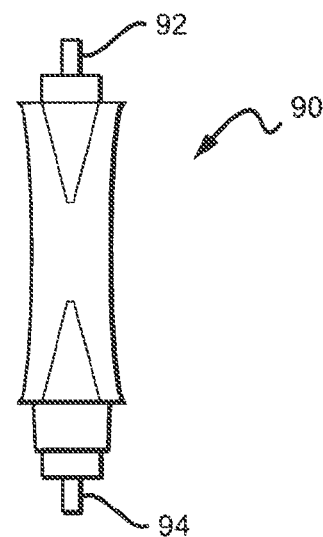
FIG. 18 is another embodiment of a hand pump for use with a corporeal drainage system, the hand pump having a tubular configuration.

FIGS. 17-18 illustrate another embodiment of a pump utilized in a corporeal drainage system. In this embodiment, the pump is in the form of a small hand pump (which may be made small enough in size to be considered a "finger pump") with a rebound area that is able to generate a large suction with a relatively small force. FIG. 17A-C illustrate embodiments of a small hand pump having a bulbous configuration. In FIG. 17A, the pump 80 includes a configuration with luer-type connectors at proximal and distal ends to facilitate attachment of the pump in-line to connect a connection tube and fluid receptacle, a connection tube and an implanted catheter, etc. The pump 80 includes two unidirectional valves, one at the proximal end and one at the distal end, to provide the ability of creating a negative pressure in a corporeal drainage system. The body 82 of the pump 80 can be made of a flexible material, such as, for example, silicone. FIGS. 17B and 17C illustrate two variations of the body 82 of the pump 80, FIG. 17B having a configuration in which the largest diameter of the bulb body 84 is positioned nearer the proximal end than the distal end, and FIG. 17C having a symmetrical configuration in which the largest diameter of the bulb body 84 is approximately equidistant from the proximal and distal ends. FIG. 18 illustrates a tubular-shaped hand pump 90, requiring a minimal force to begin fluid flow. To initiate fluid flow using hand pump 90, a user grasps between fingers (e.g., between the thumb and index finger) and squeezes one or more times. In one embodiment, hand pump 90 has a length in the range of approximately 1 in. to approximately 6 in. and a diameter in the range of approximately 0.25 in. to approximately 2 in. While hand pumps 80 and 90 are shown in particular configurations, it should be appreciated that many sizes and shapes are possible and would be within the scope of this invention.

Figure 19:
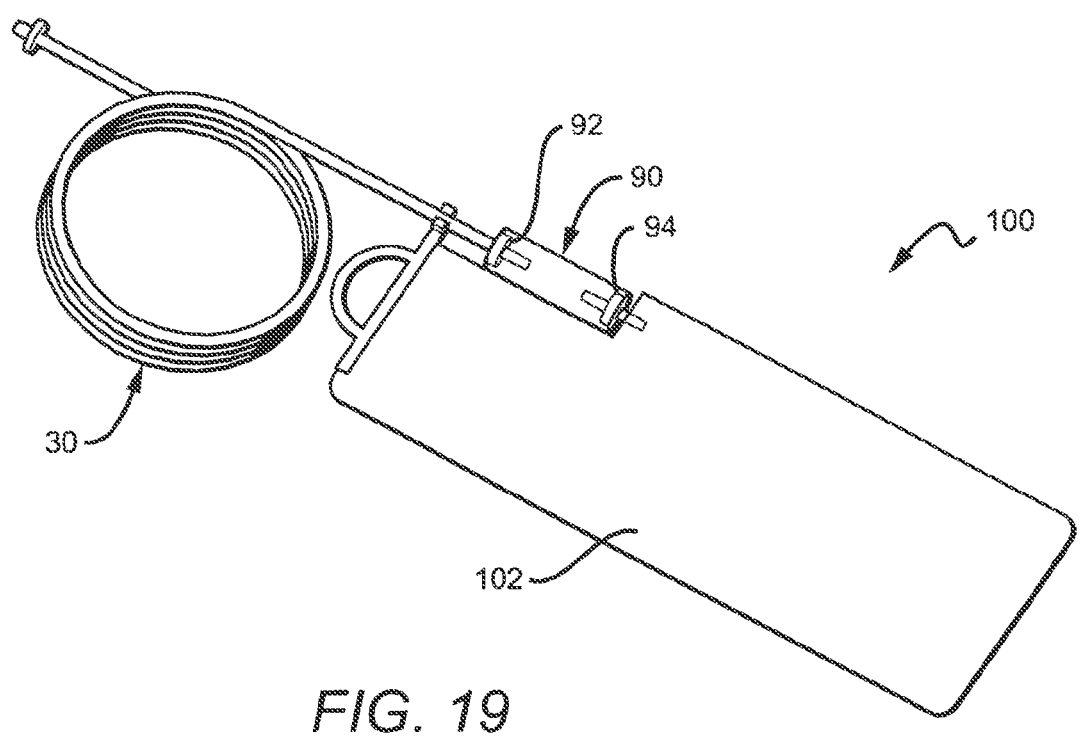
FIG. 19 is one embodiment of a corporeal drainage system, incorporating the hand pump of FIG. 18.

The hand pumps 80 and 90 can be placed in-line into a system, connecting the connection tube 30 to either a reusable container with a disposable bag therein, a disposable bottle, or a disposable bag (e.g., zero volume collapsed bag), as described above. In one embodiment, the hand pump 90 is incorporated into system 100, as illustrated in FIG. 19. A pair of one-way check valves 92, 94 respectively connect the hand pump 90 to the connection tube 30 and the fluid receptacle 102 (e.g., container, bottle, bag, etc.). In this embodiment, the hand pump 90 is includes a body made from a material that is transparent. Thus, by placing the hand pump 90 in-line in system 100, the pump 90 also acts as a "drip chamber" so that the user is able to visually monitor the flow of fluid from the bodily cavity to the fluid receptacle 102. Operation of system 100 includes first activating the hand pump 90 by squeezing the sides together and subsequently releasing one or more times (e.g., five or six times), which creates a negative pressure in the connection tube 30 as air is transported through the one-way check valves 92, 94 in a direction toward the fluid receptacle 102 until fluid begins flowing therein. Thereafter, as explained above in connection with a passive siphoning process, the fluid receptacle 102 is dropped to a level below the bodily cavity being drained (e.g., placed on the floor). The minimal force required to begin fluid flow in system 100 as described is advantageous to the target user due to strength and stamina concerns discussed above. The relative small size of the system (especially in the case that the system includes a zero volume collapsed bag) facilitates shipping and storage.

Figure 20:
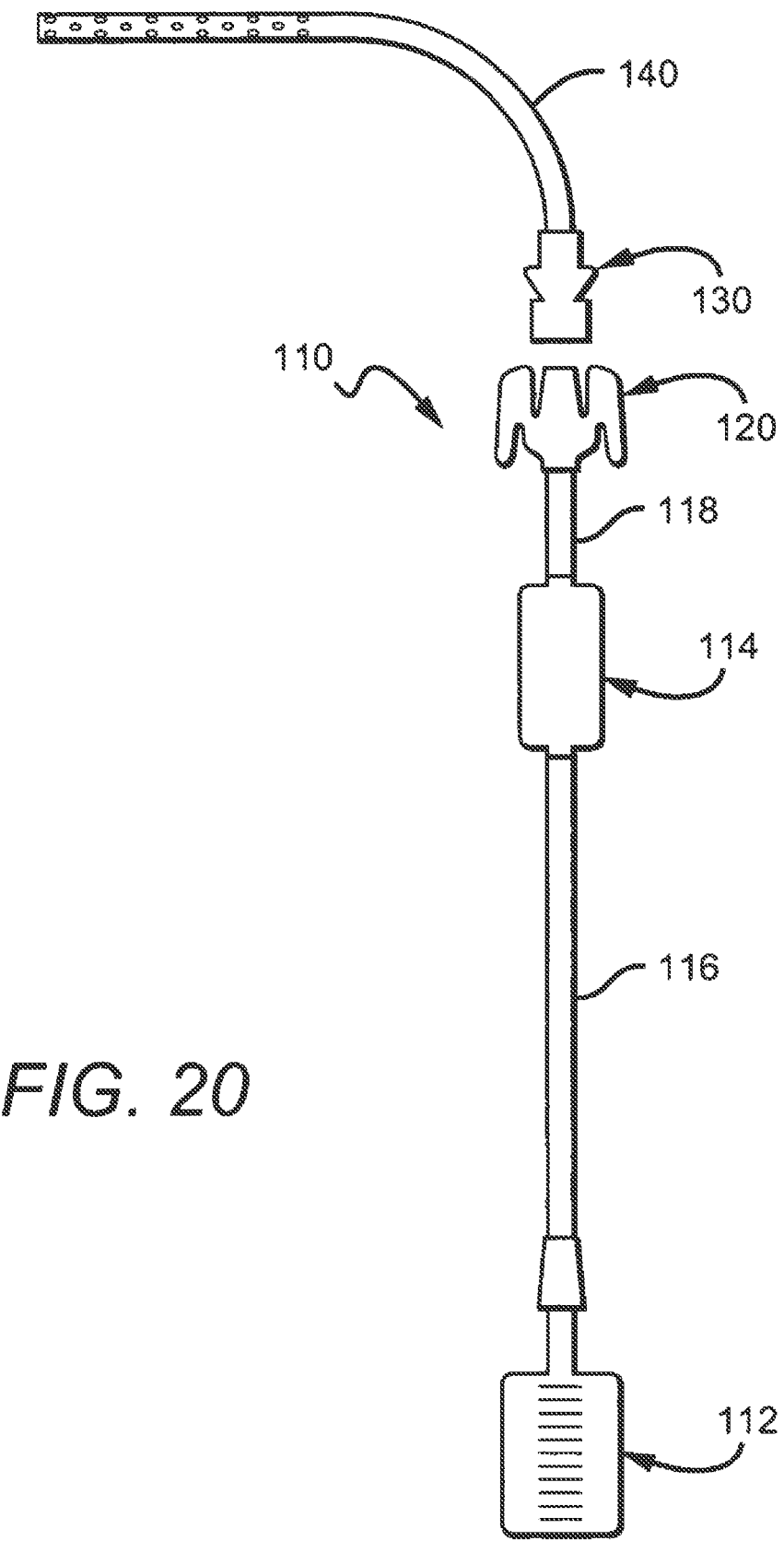
FIG. 20 is one embodiment of a corporeal drainage system, illustrating a connection system between an implanted catheter and a fluid flow conduit.

As discussed above, the corporeal drainage system may include a connection system for easy, fast and secure connection between an implanted catheter and a connection tube as described herein (e.g., connection tube 30). Particular connection systems for the corporeal drainage system described herein are disclosed in commonly owned U.S. Provisional Application No. 60/720,443, filed Sep. 26, 2005, entitled "Catheter Connection System," the complete contents of which are expressly incorporated by reference as if fully set forth herein. One example of a corporeal drainage system incorporating a catheter connection system is illustrated in FIG. 20, which shows corporeal drainage system 110 prior to the initiation of a drainage process, including fluid receptacle 112, pump 114, first fluid flow conduit 116, connecting the pump 14 to the fluid receptacle 112, second fluid flow conduit 118, and drainage line connector 120. A catheter connector 130 is connected to an implanted catheter 140, the catheter connector 130 and drainage line connector 120 being configured to fluidly connect second conduit 118 to catheter 140, as described more completely in commonly owned U.S. Provisional Application No. 60/720,443. To utilize the corporeal drainage system 110, the connection between the catheter connector 120 and drainage line connector 130 is first established, followed by activation of the system by priming (e.g., squeezing) the pump 114 one or more times to initiate fluid flow from a bodily cavity. The fluid receptacle 112 is either initially positioned below the cavity to be drained or is positioned below the cavity to be drained following activation of the system.

Figure 21:
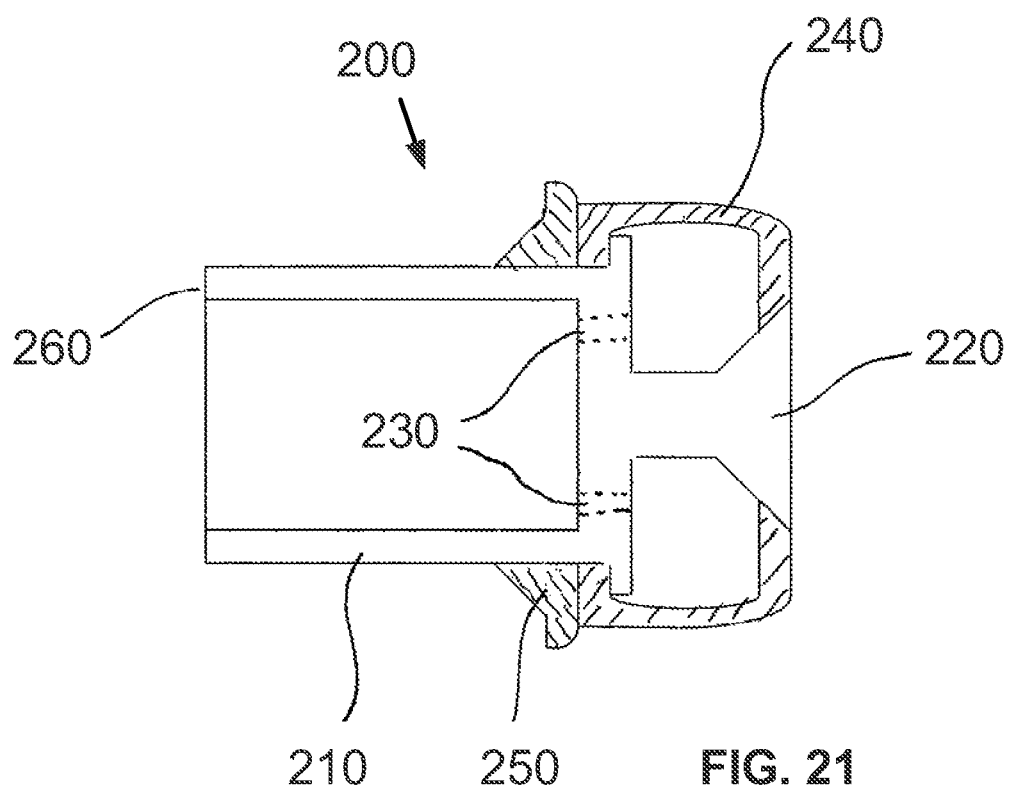
FIGS. 21-26 illustrate various examples of connection systems for use with a corporeal drainage system.
Figure 22:
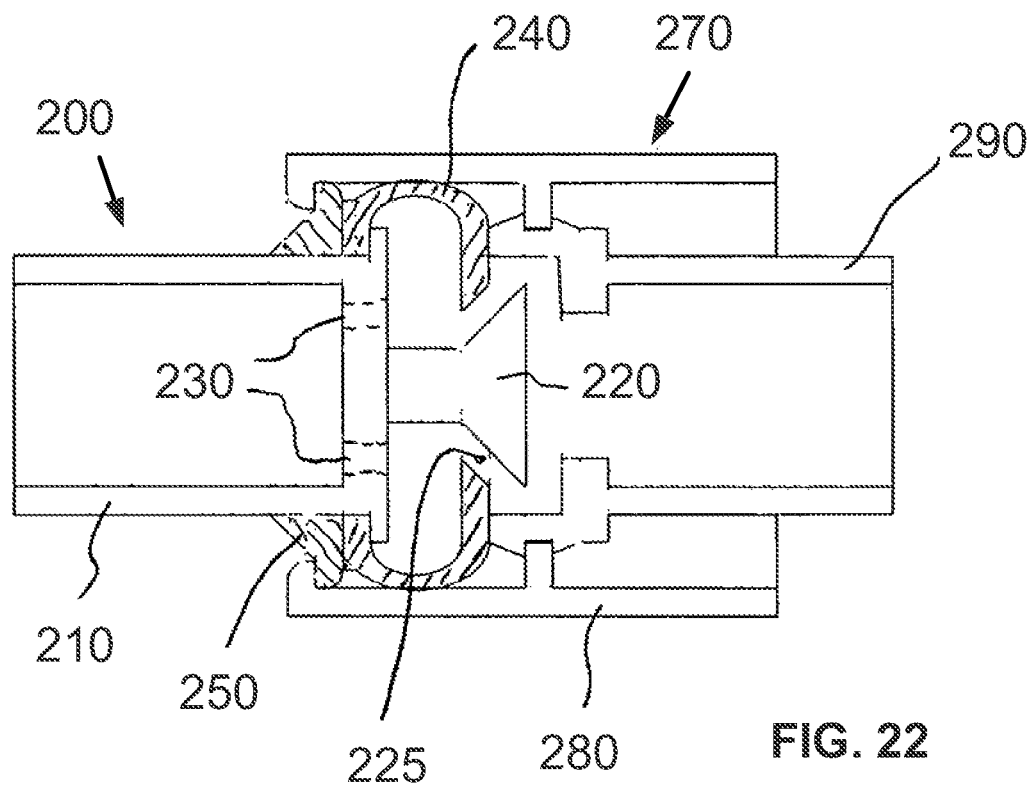

FIGS. 21-22 illustrate a connection system according to one embodiment. FIG. 21 shows a catheter connector 200 including a body 210 defining a tapered feature 220 and flow apertures 230. A sealing element 240 is provided to abut the tapered feature 220 to effectively seal the flow apertures 230. A retaining element 250 may be provided to resist movement of the sealing element 240 toward a distal end 260 of the body 210. FIG. 22 shows the catheter connector 200 coupled to a drainage line connector 270. The drainage line connector 270 includes a positioning sleeve 280 and an actuating member 290 so that when the drainage line connector 270 is connected to the catheter connector 200, the actuating member 290 deforms the sealing element 240 away from the tapered feature 220 and allows fluid flow through a gap 225 there between.

Figure 23:
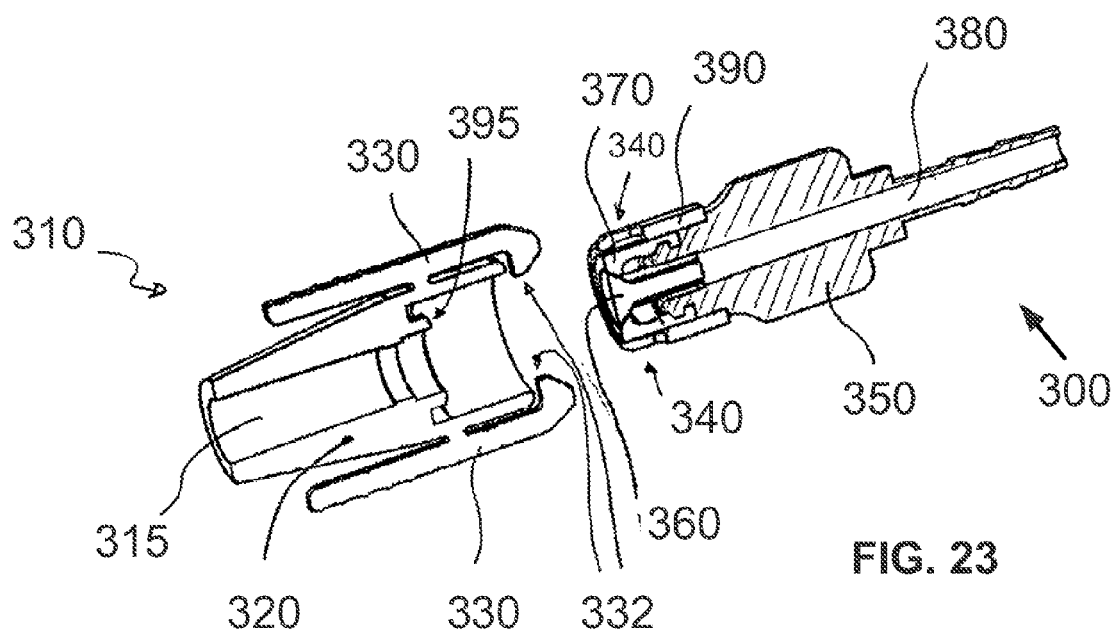
Figure 24:
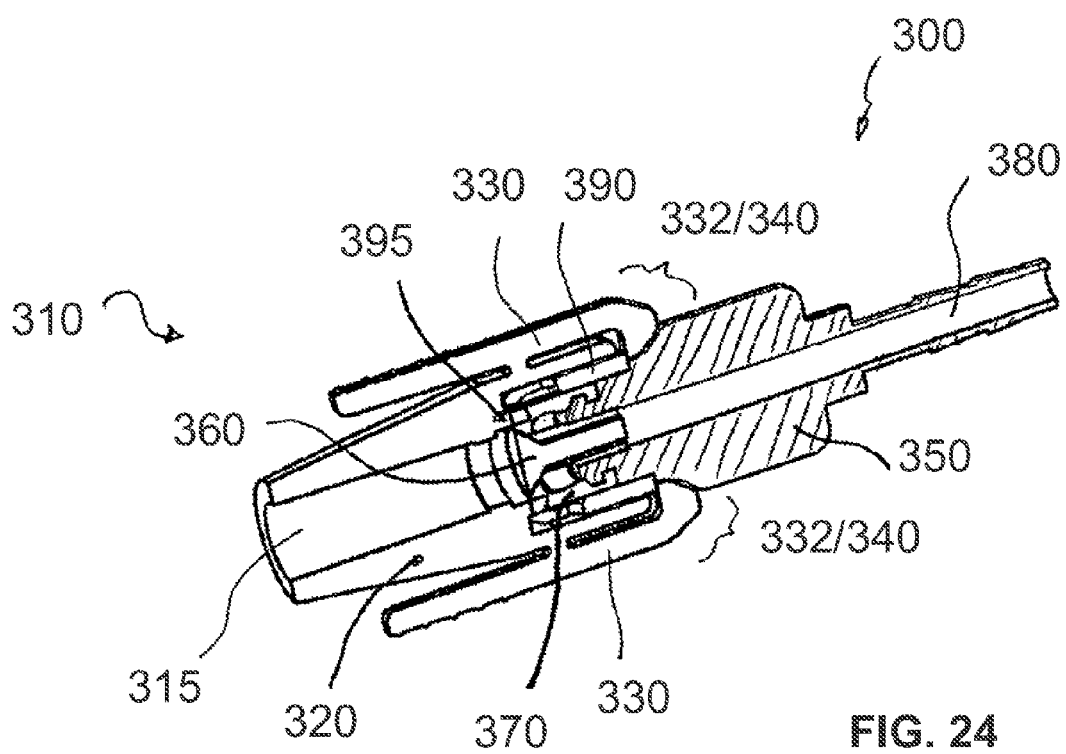

FIGS. 23-24 illustrate another example of a connection system comprising a sealing element positioned between at least two components, wherein the components are coupled to one another by at least one hinge clip. The connection system includes a catheter connector 300 and a drainage line connector 310. The drainage line connector 310 comprises a drain body 320 including hinge clips 330 pivotably affixed to the drain body 320. Each of the hinge clips 330 include an engagement feature 332 configured to engage a complimentary coupling feature 340 of the catheter connector 300. As shown in FIG. 23, the catheter connector 300 may include a plug body 350 that defines a tapered feature 360. In one embodiment, the tapered feature 360 is formed separately from the plug body 350. In such a configuration, tapered feature 360 may be affixed (e.g., adhesively bonded, ultrasonically welded, solvent welded, or otherwise affixed) to the plug body 350. In another embodiment, the tapered feature 360 may be formed integrally or monolithically with the plug body 350. A sealing element 370 may abut the tapered feature 360 to effectively seal a bore 380 of the sealing plug body 350 at one end. A retaining sleeve 390 may facilitate coupling of the deformable sealing element 370 to the sealing plug body 350. Also, the retaining sleeve 390 may extend beyond the deformable sealing element 370 and the tapered feature 360 toward the drainage line connector 310. Such a configuration may inhibit inadvertently deforming the deformable sealing element 370. The drainage line connector 310 may include an actuating member 395 configured to deform the deformable sealing element 370 upon assembly of the drainage line connector 310 and the catheter connector 300 (see FIG. 24). As shown in FIG. 24, the actuating member 395 may abut and deform the sealing element 370 away from the tapered feature 360 to allow for fluid flow from the bore 380 of the catheter connector 300 to a bore 315 of the drainage line connector 310.

Figure 25:
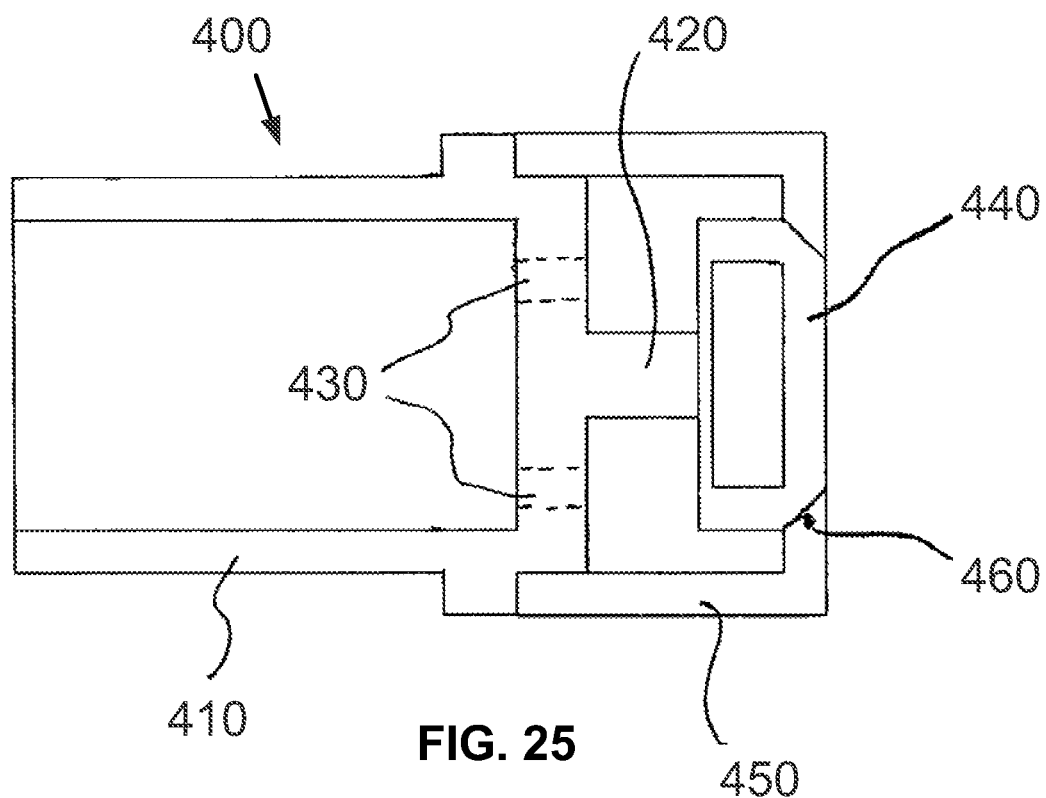
Figure 26:
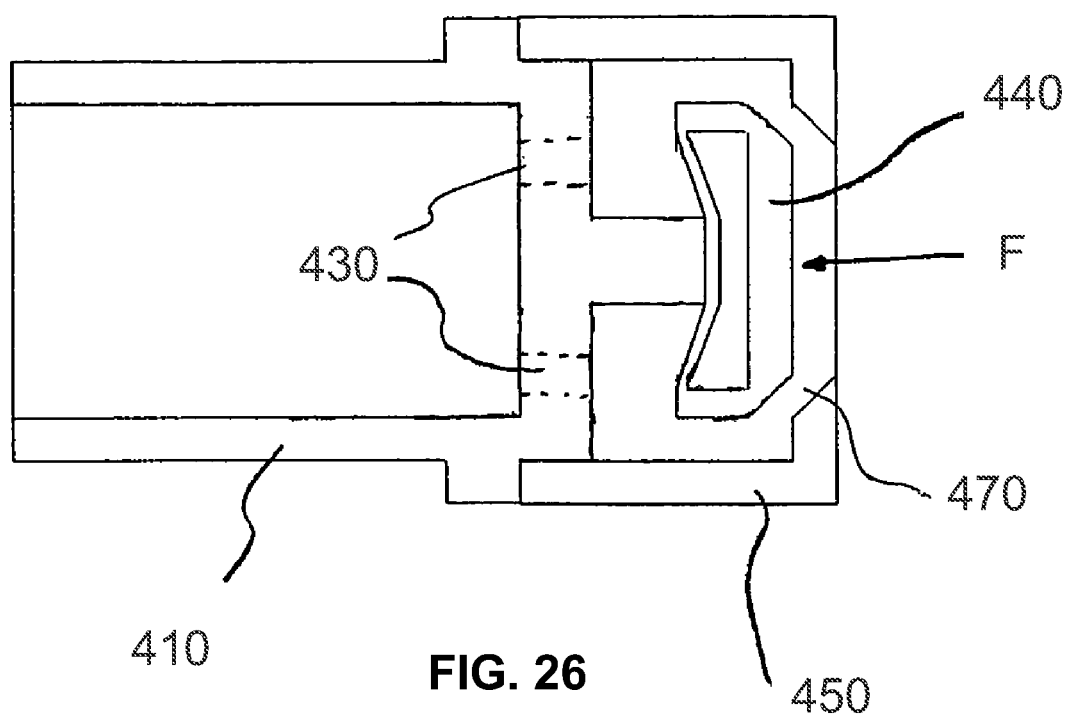

FIGS. 25-26 illustrate yet another example of a connection system comprising a catheter connector 400 including a body 410 defining a protruding feature 420, apertures 430, and a sealing element 440 positioned between the protruding feature 420 and a closure element 450. The sealing element 440 forms a seal along a mating surface 460 defining an aperture through the closure element 450. A force F (e.g., generated by an actuating member of a drainage line connector) may be applied to at least a portion of the sealing element 440 to deform the sealing element 440 and allow fluid to flow through a gap 470 formed between the sealing element 440 and the closure element 450.

In another embodiment of a corporeal drainage system, the drainage line connector 130 is attached to a connection tube, such as connection tube 30, which is connected to a fluid receptacle that also acts as a pump for the system (i.e., the initiator of negative pressure), such as illustrated in FIGS. 4-6, 7-13 and 14-16 and described above. Use of such a system would begin with attachment of the drainage line connector 130 to the catheter connector 120, followed by activation of the system, as described herein.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A method of draining fluid from a bodily cavity, comprising:
    providing a corporeal drainage system including a flexible connection tube and a fluid receptacle having only one opening to an interior thereof, the opening in fluid communication with the connection tube, the fluid receptacle having an initial rest state in a fully or approximately fully collapsed configuration before any force is applied;
    further including a first activation member and a second activation member;
    creating a negative pressure by transitioning the fluid receptacle from the collapsed configuration to an expanded configuration, the transitioning including activating the first and second activation members; and
    drawing fluid from the bodily cavity into the connection tube.

2. The method according to claim 1, wherein the transitioning further comprises placing the fluid receptacle at a level below the bodily cavity.

3. The method according to claim 1, wherein the activating includes pulling two opposing sides of the fluid receptacle away from one another.

4. The method according to claim 1, wherein the first and second activation members are configured to move orthogonal to a central axis of the connection tube.

5. The method according to claim 1, wherein the fluid receptacle comprises flexible side walls, the method further comprising connecting the connection tube to the fluid receptacle on a side edge of the flexible side walls.

6. The method according to claim 1, wherein the connection tube is connected to a catheter.

* * * * *